United States Patent
Yoder et al.

(10) Patent No.: US 11,739,293 B2
(45) Date of Patent: Aug. 29, 2023

(54) METHOD FOR GENERATING MESODERM AND/OR ENDOTHELIAL COLONY FORMING CELL-LIKE CELLS HAVING IN VIVO BLOOD VESSEL FORMING CAPACITY

(71) Applicant: Indiana University Research and Technology Corporation, Indianapolis, IN (US)

(72) Inventors: Mervin C. Yoder, Indianapolis, IN (US); Nutan Prasain, Marlborough, MA (US)

(73) Assignee: Indiana University Research and Technology Corporation, Bloomington, IN (US)

( * ) Notice: Subject to any disclaimer, the term of this patent is extended or adjusted under 35 U.S.C. 154(b) by 699 days.

(21) Appl. No.: 16/323,722

(22) PCT Filed: Aug. 4, 2017

(86) PCT No.: PCT/US2017/045496
§ 371 (c)(1),
(2) Date: Feb. 6, 2019

(87) PCT Pub. No.: WO2018/031404
PCT Pub. Date: Feb. 15, 2018

(65) Prior Publication Data
US 2019/0211304 A1 Jul. 11, 2019

Related U.S. Application Data

(60) Provisional application No. 62/372,907, filed on Aug. 10, 2016.

(51) Int. Cl.
*C12N 5/0735* (2010.01)
*C12N 5/071* (2010.01)
*A61K 35/12* (2015.01)

(52) U.S. Cl.
CPC ............ *C12N 5/0606* (2013.01); *A61K 35/12* (2013.01); *C12N 5/069* (2013.01); *C12N 2501/115* (2013.01); *C12N 2501/155* (2013.01); *C12N 2501/16* (2013.01); *C12N 2501/165* (2013.01); *C12N 2501/65* (2013.01); *C12N 2506/02* (2013.01); *C12N 2506/03* (2013.01); *C12N 2506/45* (2013.01); *C12N 2533/54* (2013.01)

(58) Field of Classification Search
None
See application file for complete search history.

(56) References Cited

U.S. PATENT DOCUMENTS 10,563,175 B2 * 2/2020 Yoder ..................... A61P 11/00
2010/0261274 A1 10/2010 Vodyanyk et al.
2010/0261276 A1 10/2010 Park et al.
2015/0329821 A1 11/2015 Agency
2016/0194610 A1 7/2016 Slukvin et al.

FOREIGN PATENT DOCUMENTS

WO 2010011352 A2 1/2010
WO 2015138634 A1 9/2015

OTHER PUBLICATIONS

Wanjare M, Kusuma S, Gerecht S. Defining differences among perivascular cells derived from human pluripotent stem cells [published correction appears in Stem Cell Reports. May 6, 2014;2(5):746], Stem Cell Reports. 2014;2(5):561-575. (Year: 2014).*
Wanjare et al. Supplementary figures (Year: 2014).*
Yao S. MicroRNA biogenesis and their functions in regulating stem cell potency and differentiation. Biol Proced Online. Mar. 9, 2016; 18:8. (Year: 2016).*
Liu B, Li J, Cairns MJ. Identifying miRNAs, targets and functions. Brief Bioinform. Jan. 2014;15(1):1-19. (Year: 2014).*
Zhou Y, Yang F, Chen T, Wu Y, Yang M, Zhu J, Zhang L. An updated view on the differentiation of stem cells into endothelial cells. Sci China Life Sci. Aug. 2014;57(8):763-73. (Year: 2014).*
Jin HY, Gonzalez-Martin A, Miletic AV, Lai M, Knight S, Sabouri-Ghomi M, Head SR, Macauley MS, Rickert RC, Xiao C. Transfection of microRNA Mimics Should Be Used with Caution. Front Genet. Dec. 2, 2015;6:340 (Year: 2015).*
Prasain et al. Differentiation of human pluripotent stem cells to cells similar to cord-blood endothelial colony-forming cells. Nat Biotechnol. Nov. 2014;32(11):1151-1157. (Year: 2014).*
Evseenko D, Zhu Y, Schenke-Layland K, Kuo J, Latour B, Ge S, Scholes J, Dravid G, Li X, MacLellan WR, Crooks GM. Mapping the first stages of mesoderm commitment during differentiation of human embryonic stem cells. Proc Natl Acad Sci USA. Aug. 3, 2010;107(31):13742-7. (Year: 2010).*
Vodyanik MA, Yu J, Zhang X, Tian S, Stewart R, Thomson JA, Slukvin II. A mesoderm-derived precursor for mesenchymal stem and endothelial cells. Cell Stem Cell. Dec. 3, 2010;7(6):718-29. (Year: 2010).*

(Continued)

*Primary Examiner* — Emily A Cordas
(74) *Attorney, Agent, or Firm* — Faegre Drinker Biddle & Reath LLP

(57) ABSTRACT

The present disclosure relates generally to methods and compositions useful in cell and tissue biology and therapeutics. In particular, an in vitro method for differentiating pluripotent stem cells into KDR$^+$NCAM$^+$APLNR$^+$ mesoderm cells and/or SSEA5$^-$KDR$^+$NCAM$^+$APLNR$^+$ mesoderm cells is provided. The disclosed mesoderm cells may be used to generate blood vessels in vivo and/or further differentiated in vitro into endothelial colony forming cell-like cells (ECFC-like cells). Purified human cell populations of KDR$^+$NCAM$^+$APLNR$^+$ mesoderm cells and ECFC-like cells are provided. Test agent screening and therapeutic methods for using the cell populations of the present disclosure are provided.

10 Claims, 16 Drawing Sheets

(56) References Cited

OTHER PUBLICATIONS

Tang C, Lee AS, Volkmer JP, Sahoo D, Nag D, Mosley AR, Inlay MA, Ardehali R, Chavez SL, Pera RR, Behr B, Wu JC, Weissman IL, Drukker M. An antibody against SSEA-5 glycan on human pluripotent stem cells enables removal of teratoma-forming cells. Nat Biotechnol. Aug. 14, 2011;29(9):829-34 (Year: 2011).*

Van Balkom et al. Endothelial cells require miR-214 to secrete exosomes that suppress senescence and induce angiogenesis in human and mouse endothelial cells. Blood. May 9, 2013;121(19):3997-4006, S1-15. (Year: 2013).*

International Search Report and Written Opinion issued by the ISA/US Commissioner for Patents, dated Nov. 6, 2017, for International Application No. PCT/US2017/045496; entire document.

Calloni et al., "Reviewing and Updating the Major Molecular Markers for Stem Cells," Stem Cells and Development, Jan. 22, 2013, vol. 22, No. 9, pp. 1455-1476; entire document.

International Preliminary Report on Patentability received for PCT Patent Application No. PCT/US17/45496, dated Feb. 21, 2019, 8 pages.

International Search Report and Written Opinion received for PCT Patent Application No. PCT/US17/45496, dated Nov. 6, 2017, 9 pages.

Prasain, Nutan et al., "Differentiation of human pluripotent stem cells to cells similar to cord-blood endothelial colony-forming cells", Nature Biotechnology, vol. 32, No. 11, Oct. 12, 2014, pp. 1151-1157, XP055383069, ISSN: 1087-0156, DOI: 10.1038/nbt.3048.

Yoder, "Differentiation of pluripotent Stem cells into endothelial cells", Curr. Opin. Hematol., vol. 32, No. 11, May 2015, pp. 1-10.

* cited by examiner

Day 4 differentiated cells

APLNR⁻ mesoderm cells          APLNR⁺ mesoderm cells 3 inhibitors: miR-221-3p, miR-1271-5p, miR-559
3 mimics: miR-330-5p, miR-145-5p, miR-214-3p
3m3i: 3 inhibitors and 3 mimics

METHOD FOR GENERATING MESODERM AND/OR ENDOTHELIAL COLONY FORMING CELL-LIKE CELLS HAVING IN VIVO BLOOD VESSEL FORMING CAPACITY

CROSS REFERENCE TO PRIOR APPLICATIONS

This application claims the benefit of U.S. Provisional Patent Application Ser. No. 62/372,907, filed Aug. 10, 2016, which is incorporated herein by reference as if set forth in its entirety.

FIELD OF THE DISCLOSURE

The present disclosure relates to the fields of cell and tissue biology. More particularly, the present disclosure relates to lineage-specific differentiation of pluripotent stem cells into mesoderm cells and/or endothelial colony forming cell-like cells (ECFC-like cells) that can form blood vessels in vivo.

BACKGROUND OF THE DISCLOSURE

Endothelial colony forming cells (ECFCs) are rare circulating endothelial cells, particularly abundant in umbilical cord blood, with clonal proliferative potential and intrinsic in vivo vessel forming ability (Yoder, M. C. et al. *Blood* 109, 1801-1809 (2007); Ingram, D. A. et al. *Blood* 105, 2783-2786 (2005); Ingram, D. A. et al. *Blood* 104, 2752-2760 (2004); Critser, P. J. et al. *Microvasc Res* 80, 23-30 (2010); Au, P. et al. *Blood* 111, 1302-1305 (2008); Melero-Martin, J. M. et al. *Circ Res* 103, 194-202 (2008)). It is not understood what type of cell within umbilicial cord blood or donor marrow gives rise to ECFCs. When cultured primary ECFCs are injected intravenously into rodent vascular injury models, they are recruited the site of vascular injury or tissue ischemia to orchestrate initiation of a vasculogenic response (Moubarik, C. et al. *Stem Cell Rev* 7, 208-220 (2011); Schwarz, T. M. et al. *Arterioscler Thromb Vasc Biol* 32, e13-21 (2012); Saif, J. et al. *Arterioscler Thromb Vasc Biol* 30, 1897-1904 (2010). Human ECFCs have been reported to enhance vascular repair and improve blood flow following myocardial infarction (Dubois, C. et al. *J Am Coll Cardiol* 55, 2232-2243 (2010); Schuh, A. et al. *Basic Res Cardiol* 103, 69-77 (2008), stroke (Moubarik, C. et al. 2011), ischemic retinopathy (Stitt, A. W. et al. *Prog Retin Eye Res* 30, 149-166 (2011); Medina, R. J. et al. *Invest Ophthalmol Vis Sci* 51, 5906-5913 (2010), ischemic limb injury (Schwartz et al. 2012; Saif et al. 2010; Bouvard, C. et al. *Arterioscler Thromb Vasc Biol* 30, 1569-1575 (2010); Lee, J. H. et al. *Arterioscler Thromb Vasc Biol* (2013), and to engraft and re-endothelialize denuded vascular segments or implanted grafts; (Stroncek, J. D. et al. *Acta Biomater* 8, 201-208 (2012). In subjects with peripheral arterial disease (PAD) and critical limb ischemia (CLI), circulating or resident ECFCs may become prone to replicative senescence (i.e., ECFCs may lack proliferative potential), thus rendering them impotent for autologous vascular repair. At least for these reasons, it is desirable to find alternate sources of ECFCs or other cell types that may be used for vascular repair.

Human pluripotent stem cells (hPSCs) display virtually unlimited self-renewal capacity and ability to differentiate into any cell type in the animal body (Robbins, R. D. et al. *Curr Opin Organ Transplant* 15, 61-67 (2010); Broxmeyer, H. E. et al. *Blood* 117, 4773-4777 (2011); Lee, M. R. et al. *Stem Cells* 31, 666-681 (2013). The present inventors have previously determined a method for in vitro derivation of ECFC-like cells from hPSCs, in which the ECFC-like cells can form blood vessels in vivo (PCT/US2015/020008).

It is desirable to mitigate and/or obviate one or more of the above deficiencies.

SUMMARY OF THE DISCLOSURE

The present disclosure is broadly summarized as relating to methods for generating lineage-specific mesoderm cells and/or endothelial colony forming cell-like cells (ECFC-like cells) from hPSCs. Protocols for reproducibly differentiating hPSCs into populations of lineage-specific mesoderm and/or ECFC-like cells having in vivo blood vessel formation capacity are provided In an aspect, the present disclosure provides a method for generating an isolated population of human $KDR^+NCAM^+APLNR^+$ mesoderm cells from human pluripotent stem cells. The method comprises providing pluripotent stem cells (PSCs); inducing the pluripotent stem cells to undergo mesodermal differentiation, wherein the mesodermal induction comprises: i) culturing the pluripotent stem cells for about 24 hours in a mesoderm differentiation medium comprising Activin A, BMP-4, VEGF and FGF-2; and ii) replacing the medium of step i) with a mesoderm differentiation medium comprising BMP-4, VEGF and FGF-2 about every 24-48 hours thereafter for about 72 hours; and isolating from the cells induced to undergo differentiation the mesoderm cells, wherein the isolation of mesoderm cells comprises: iii) sorting the mesoderm cells to select for $KDR^+NCAM^+APLNR^+$ cells.

In an embodiment, the sorting further comprises selection of $SSEA5^-KDR^+NCAM^+APLNR^+$ cells.

In an embodiment, the mesodermal induction further comprises contacting the cells undergoing mesodermal induction with Fc-NRP-1. In an embodiment, the mesoderm differentiation medium of step ii).

In an embodiment, the mesodermal induction further comprises contacting the cells undergoing mesodermal induction with one or more miRNA inhibitor, wherein the one or more miRNA inhibitor inhibits an miRNA that exhibits decreased expression in $SSEA5^-KDR^+NCAM^+APLNR^+$ mesoderm cells relative to PSCs. In an embodiment, the miRNA inhibitor inhibits an miRNA selected from the group consisting of: miR-221-3p, miR-1271-5p, miR-559, miR543, miR-361-3p, miR-30d-5p, miR-124-3p and miR-185-5p. In an embodiment, the cells undergoing mesodermal induction are contacting with one or more of an miRNA inhibitor of miR-221-3p, miR-1271-5p and miR-559, preferably miR-221-3p.

In an embodiment, the mesodermal induction further comprises contacting the cells undergoing mesodermal induction with one or more miRNA mimic, wherein the one or more miRNA mimic mimics an miRNA that exhibits increased expression in $SSEA5^-KDR^+NCAM^+APLNR^+$ mesoderm cells relative to PSCs. In an embodiment, the miRNA mimic mimics an miRNA selected from the group consisting of: miR-330-5p, miR-145-5p, miT-214-3p and miR-497-5p. In an embodiment, the cells undergoing mesodermal induction are cultured with one or more of an miRNA mimic of miR-330-5p, miR-145-5p and miT-214-3p, preferably miR-330-5p. In an embodiment, the mesodermal induction further comprises contacting the cells undergoing mesodermal induction with a miR-214 mimic.

In an embodiment, the isolated mesoderm cells have a capacity to form blood vessels when implanted into a mammal.

In an embodiment, the method further comprises: inducing the isolated mesoderm cells to undergo endothelial differentiation, wherein the endothelial induction comprises: culturing the isolated mesoderm cells in an endothelial differentiation medium comprising BMP-4, VEGF and FGF-2 for about 6-8 days; and isolating from the cells induced to undergo endothelial differentiation endothelial colony forming-like (ECFC-like) cells, wherein the ECFC-like cells are CD31+NRP-1+ and exhibit a cobblestone morphology.

In an embodiment, the isolated ECFC-like cells are further characterized by one or more of CD144+, KDR+ and α-SMA-expression.

In an embodiment, the endothelial inducing step is carried out in the absence of one or more of: co-culture cells, embryoid body formation and exogenous TGF-β inhibition.

In an embodiment, the isolated ECFC-like cells have a capacity to form blood vessels when implanted into a mammal in the absence of co-implanted cells.

In an aspect, an isolated population of human $KDR^+NCAM^+APLNR^+$ mesoderm cells is provided. The isolated $KDR^+NCAM^+APLNR^+$ mesoderm cells have a capacity to form blood vessels when implanted into a mammal and wherein the isolated $KDR^+NCAM^+APLNR^+$ mesoderm cells were derived in vitro from human pluripotent stem cells.

In an embodiment, the $KDR^+NCAM^+APLNR^+$ mesoderm cells are $SSEA5^-$. In an embodiment, the $KDR^+NCAM^+APLNR^+$ mesoderm cells exhibit increased expression of one or more lateral plate-extra-embryonic mesoderm markers relative to PSCs, wherein the lateral plate-extra-embryonic mesoderm markers are selected from BMP4, WNT5A, NKX2-5 and HAND1. In an embodiment, the $KDR^+NCAM^+APLNR^+$ mesoderm cells lack increased expression of one or more axial mesoderm markers, paraxial mesoderm markers and/or intermediate mesoderm markers, relative to PSCs, wherein the axial mesoderm markers are selected from CHIRD and SHH, the paraxial mesoderm markers are selected from PAX1, MEOX1, and TCF15, and the intermediate mesoderm markers are selected from GOSR1, PAX2 and PAX8.

In an aspect, an isolated population of human $KDR^+NCAM^+APLNR^+$ mesoderm cells obtained according to the method provided herein is provided.

In an aspect, an isolated population of human NRP-1+ CD31+ endothelial colony forming cell-like cells (ECFC-like cells) obtained according to the method provided herein is provided.

In an aspect, a pharmaceutical composition comprising the $KDR^+NCAM^+APLNR^+$ mesoderm cells provided herein is provided.

In an aspect, a pharmaceutical composition comprising the endothelial colony forming cell-like cells (ECFC-like cells) provided herein is provided.

In another aspect of the present disclosure, there is provided a method for transplantation in a subject in need thereof, the method comprising providing to the subject an isolated population of cells as described herein.

In another aspect of the present disclosure, there is provided a method of treating a subject in need of epithelial repair, the method comprising providing to the subject a therapeutically effective amount of a population of cells as described herein.

In another aspect of the present disclosure, there is provided a pharmaceutical composition comprising mesoderm and/or ECFC-like cells obtained by a method as described herein.

In another aspect of the present disclosure, there is provided a method of examining a test agent for its ability to modify cellular activity, the method comprising:
  exposing at least one of the cells of the population of cells as described herein to a test agent and;
  observing the effect of the test agent on one or more of cell growth and cell viability.

BRIEF DESCRIPTION OF THE DRAWINGS

The patent or application file contains at least one drawing in color. Copies of this patent or patent application publication with color drawings will be provided by the Office upon request and payment of the necessary fee.

The features of the disclosure will become more apparent in the following detailed description in which reference is made to the appended drawings wherein:

FIG. 1A depicts a schematic of a one-step, 2D, serum and feeder-free mesoderm lineage differentiation protocol.

FIG. 1B depicts a sorting strategy for day 4 differentiated hiPSCs.

FIG. 1C depicts a strategy for sorting $KDR^+NCAM^+APLNR^+$ ($K^+N^+A^+$), $KDR^+NCAM^+APLNR^-$ ($K^+N^+A^-$), and $KDR^+NCAM^-APLNR^-$ ($K^+N^-A^-$) cells and further differentiating and examining the emergence of NRP-$1^+CD31^+$ ECFC-like cells.

FIG. 1D depicts examination of sorted $K^+N^+A^+$, $K^+N^+A^-$ and $K^+N^-A^-$ mesoderm sub-sets that were further differentiated into an ECFC-like lineage for another 9 days (3 plus 9 days, total of 12 days) for the emergence of NRP-$1^+CD31^+$ cells at 8, 10 and 12 days of differentiation (three left-most panels); morphology of day 12 monolayers is shown (fourth panel from left), α-SMA expression is shown (fifth panel from left); and expression of CD31 and CD144 endothelial markers is shown (right-most panels).

FIG. 1E depicts a bar graph showing that hiPSC-ECFC-like cells, $K^+N^+A^+$-, $K^+N^+A^-$-, and $K^+N^-A^-$-mesoderm-derived NRP-$1^+CD31^+$ cells exhibited differing levels of clonal proliferative potential.

FIG. 1F depicts images of various qualities of in vivo human blood vessel formation by hiPSC-ECFC-like cells, $K^+N^+A^+$-, $K^+N^+A^-$-, and $K^+N^-A^-$-mesoderm-derived NRP-$1^+CD31^+$.

FIG. 1G depicts a bar graph showing that hiPSC-ECFC-like cells, $K^+N^+A^+$-ECFC-like cells, $K^+N^+A^-$-ECs, and $K^+N^-A^-$-ECs form various amounts of functional $hCD31^+$ vessels.

FIG. 2A illustrates that $APLNR^+$ cells were found in the $KDR^+NCAM^+$ mesoderm sub-set but not in the $KDR^-NCAM^-$ sub-set.

FIG. 2B depicts levels of $KDR^+$ cells at days 3, 4, and 5 of differentiation.

FIG. 2C depicts levels of endothelial marker (CD31, NRP-1 and CD144) expression in day 4-differentiated cells.

FIG. 3A depicts a sorting strategy for day 4-differentiated hiPSCs.

FIG. 3B shows that sorted APLNR− mesoderm cells produced a teratoma after 2 months of in vivo implantation (left panel) and APLNR+ mesoderm cells formed robust in vivo human blood vessels filled with host murine red blood cells (right panel; blue open arrows) with accompanying endoderm-derived cell like derivatives (right panel; pink closed arrows).

FIG. 4A depicts a sorting strategy for day 4 differentiated hiPSCs.

FIG. 4B depicts formation of robust functional in vivo vessels by SSEA5−KNA+ cells (blue arrows, left panel) and the absence of robust functional in vivo vessels by SSEA5−KNA− cells (white arrows, right panel).

FIG. 4C depicts a bar graph illustrating in vivo formation of functional blood vessels by SSEA5−KNA+ cells and SSEA5−KNA− cells.

FIG. 4D depicts images of NRP-1+CD31+ blood vessels formed in vivo 8 days after implantation of SSEA5−KNA+ cells.

FIG. 5A depicts gene expression analysis of lateral plate-extra-embryonic mesoderm markers, axial, paraxial and intermediate mesoderm markers in SSEA5−KNA+ cells and hiPSCs.

FIG. 5B depicts sorted SSEA5−KNA+ cells that were further differentiated into ECFC lineage for another 8 days (4 plus 8, total of 12 days); at day 12, SSEA5−KNA+ cells produced ≥3 fold more NRP-1+CD31+ cells compared to NRP-1+CD31+ cells derived from hiPSCs (without a day 4 sorting step) (left bar graph); morphology of a monolayer of NRP1+CD31+ cells derived from SSEA5−KNA+ mesoderm cells, lack of α-SMA expression (middle panels); and uniform co-expression of CD31 and CD144 endothelial markers (right panel) in the NRP1+CD31+ cells derived from SSEA5−KNA+ mesoderm cells are also shown.

FIG. 5C depicts a bar chart showing clonal proliferative potential of hiPSC-ECFC-like cells, SSEA5−KNA+ mesoderm-derived NRP-1+CD31+ cells and SSEA5−KNA− mesoderm-derived NRP-1+CD31+ cells.

FIG. 6A depicts a schematic representation of NRP-1, KDR, Fc-NRP-1, NRP-1-B and VEGF$_{165}$ functions in endothelial cells.

FIG. 6B depicts a Western blot showing KDR phosphorylation; KDR phosphorylation was observed in VEGF stimulated groups and Fc-NRP-1 dimer treatment increased phosphorylation of KDR compared to control treated cells; decreased phosphorylation was observed in NRP-1-B treated cells.

FIG. 6C depicts a Western blot showing p130$^{cas}$/Pyk2 phosphorylation; increased p130$^{cas}$/Pyk2 phosphorylation was observed in Fc-NRP-1 dimer treated cells compared to NRP-1-B treated cells.

FIG. 6D depicts gene expression analysis for various VEGF-A isoforms between hiPSCs and SSEA5−KNA+ mesoderm cells.

FIG. 6E depicts a bar chart showing VEGF production from hiPSCs and SSEA5−KNA+ mesoderm cells at day 2 and day 4 of differentiation in the presence or absence of added VEGF$_{165}$ in the culture media.

FIG. 6F depicts a schematic showing a mesoderm lineage differentiation protocol in the presence of Fc-NRP-1 dimer.

FIG. 6G depicts a bar graph showing that dimeric Fc-NRP-1 treatment of differentiating hiPSC caused more than a 2-fold increase in production of SSEA5−KNA+ mesoderm cells compared to Fc-NRP-1 untreated cells.

FIG. 7A depicts fold change in expression of various miRNAs in Day 4 SSEA5−KNA+ mesoderm cells relative to hiPSCs (indicated by 0 on Y-axis).

FIG. 7B depicts a schematic showing a mesoderm lineage differentiation protocol that involves contacting the cells undergoing mesoderm induction with specific miRNA mimics or inhibitors or both mimics and inhibitors (3m3i) or mimic/inhibitor controls.

FIG. 7C depicts a bar chart showing frequency of Day 4 SSEA5−KNA+ mesoderm cells obtained using the protocols of FIG. 7B.

FIG. 7D depicts a bar chart showing the relative expression (y-axis) of various miRNAs (x-axis) in Day 4 SSEA5−KNA+ mesoderm cells obtained using the protocols of FIG. 7B.

FIG. 7E depicts a bar chart showing the relative expression (y-axis) of various miRNAs (x-axis) in Day 4 SSEA5−KNA+ mesoderm cells obtained using the protocols of FIG. 7B.

FIG. 8A depicts bar charts showing relative expression levels (y-axis) of miR-214 (left) and its putative target CLDN6 (right) in hiPSCs and SSEA5−KNA+ mesoderm cells.

FIG. 8B depicts a bar chart showing production of SSEA5−KNA+ mesoderm cells and a GFP reporter control vector (y-axis) when miR-214 was over-expressed in cells undergoing mesodermal induction.

FIG. 8C depicts results of a luciferase reporter assay confirming that miR-214 directly regulates expression of wild type (WT) CLND6.

FIG. 8D depicts results of a differential gene expression analysis between hiPSC and SSEA5−KNA+ mesoderm cells.

DETAILED DESCRIPTION OF THE DISCLOSURE

Figure 1A:
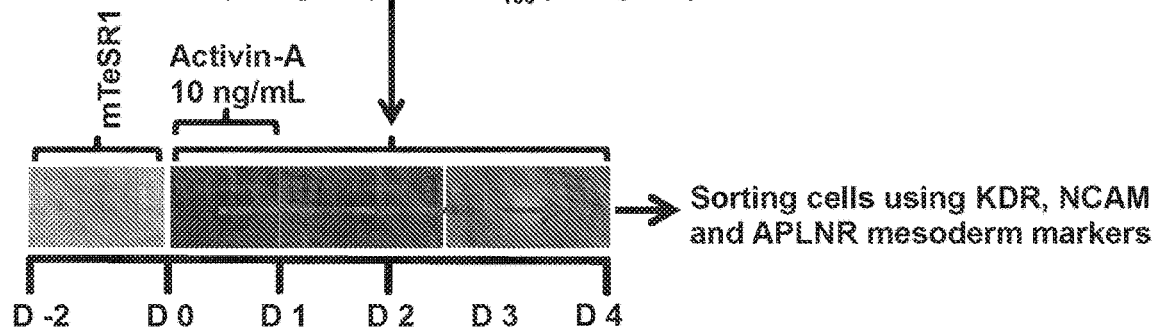
FIGS. 1A-1G illustrate that NCAM and APLNR co-expressing cells within day 4 (D4) $KDR^+$ mesoderm cells ($KNA^+$ mesoderm) give rise to NRP-$1^+CD31^+$ endothelial cells with ECFC competence.

The present disclosure generally relates to methods for in vitro differentiation of pluripotent cells, such as, for example, human embryonic stem cells (hESCs) or induced pluripotent stem cells (iPSCs) (collectively, human pluripotent stem cells (hPSCs)), into lineage-specific mesoderm cells and, optionally, further differentiating the lineage-specific mesoderm cells into endothelial colony forming cell-like cells (ECFC-like cells). Surprisingly, the inventors have found that the mesoderm cells generated and isolated using the method provided herein can generate blood vessels in vivo. In various embodiments of the method provided herein, the resulting ECFC-like cells may be further grown into blood vessels in vivo in the absence of co-culture and/or co-implantation cells.

I: Definitions

The definitions of certain terms as used in this specification are provided below. Unless defined otherwise, all technical and scientific terms used herein generally have the same meaning as commonly understood by one of ordinary skill in the art to which this disclosure belongs.

As used herein, "pluripotent cell" refers to a cell that has the potential to differentiate into any cell type, for example, cells of any one of the three germ layers: endoderm, mesoderm, or ectoderm.

As used herein, "embryonic stem cells", "ES cells" or "ESCs" refer to pluripotent stem cells derived from early embryos.

As used herein, "induced pluripotent stem cells," "iPS cells" or "iPSCs" refer to a type of pluripotent stem cell that has been prepared from a non-pluripotent cell, such as, for example, an adult somatic cell, or a terminally differentiated cell, such as, for example, a fibroblast, a hematopoietic cell, a myocyte, a neuron, an epidermal cell, or the like, by introducing into the non-pluripotent cell or contacting the non-pluripotent cell with one or more reprogramming factors.

As used herein, "mesodermal differentiation medium" refers to any nutrient medium that supports and/or enhances differentiation of pluripotent cells into cells of the mesoderm lineage.

As used herein, "mesoderm" refers to the middle of three primary germ layers in an early embryo (the other two layers being ectoderm and endoderm). There are four components or classes of mesoderm, including axial mesoderm, paraxial mesoderm, intermediate mesoderm and lateral plate/extra-embryonic mesoderm. Mesoderm comprises "mesoderm cells", also referred to as "mesodermal cells".

As used herein, miRNA mimic" refers to double-stranded RNA oligonucleotides designed to "mimic" native/endogenous miRNA activity. miRNA mimics supplement endogenous microRNA activity to discover the functional roles of individual microRNAs.

As used herein, miRNA inhibitor" refers to single-stranded RNA oligonucleotides designed to "inhibit" native/endogenous miRNA activity. miRNA inhibitors suppress the function of endogenous miRNAs, increase the expression of the target gene, and attenuate the presentation of the phenotype.

As used herein, "endothelial differentiation medium" refers to any nutrient medium that supports and/or enhances differentiation of pluripotent cells into cells of the endothelial lineage.

As used herein, "endothelial growth medium" refers to any medium that is suitable for maintaining cells of the endothelial lineage.

As used herein, "endothelial colony forming cell" and "ECFC" refer to primary endothelial cells found in the blood that display the potential to proliferate and form an endothelial colony from a single cell and have a capacity to form blood vessels in vivo in the absence of co-implanted or co-cultured cells.

As used herein, "cord blood ECFC" and "CB-ECFC" refer to primary ECFCs that are derived from umbilical cord blood.

As used herein, "endothelial colony forming cell-like cell" and "ECFC-like cell" refer to non-primary endothelial cells that are generated in vitro from human pluripotent stem cells (hPSCs). ECFC-like cells have various characteristics of ECFCs, at least including the potential to proliferate and form an endothelial colony from a single cell and have a capacity to form blood vessels in vivo in the absence of co-implanted or co-cultured cells.

As used herein, the terms "proliferation potential" and "proliferative potential" refer to the capacity of a cell to divide when provided appropriate growth promoting signals.

As used herein, the terms "high proliferation potential", "high proliferative potential" and "HPP" refer to the capacity of a single cell to divide into more than about 2000 cells in a 14 day cell culture. Preferably, HPP cells have a capacity to self-replenish. For example, the HPP-ECFC-like cells provided herein have a capacity to self-replenish, meaning that an HPP-ECFC-like cell can give rise to one or more HPP-ECFC-like cells within a secondary HPP-ECFC-like colony when replated in vitro. In some embodiments, HPP-ECFC-like cells may also have the ability to give rise to one or more of LPP-ECFC-like cells and ECFC-like cell clusters within a secondary HPP-ECFC-like colony when replated in vitro.

As used herein, the terms "low proliferation potential" "low proliferative potential" and "LPP" refer to the capacity of a single cell to divide into about 51-2000 cells in a 14 day cell culture. In some embodiments, LPP-ECFC-like cells may also have the ability to give rise to ECFC-like cell clusters. However, LPP-ECFC-like cells do not have a capacity to give rise to secondary LPP-ECFC-like cells or HPP-ECFC-like cells.

II: Methods of Differentiating Pluripotent Cells into Mesoderm Cells

In an aspect, the method provided herein involves at least three steps:

A. providing pluripotent stem cells (PSCs);

B. inducing the pluripotent stem cells to undergo mesodermal differentiation, wherein the mesodermal induction comprises: i) culturing the pluripotent stem cells for about 24 hours in a mesoderm differentiation medium comprising Activin A, BMP-4, VEGF and FGF-2; and ii) replacing the medium of step i) with a mesoderm differentiation medium comprising BMP-4, VEGF and FGF-2 about every 24-48 hours thereafter for about 72 hours; and C. isolating from the cells induced to undergo differentiation the mesoderm cells, wherein the isolation of mesoderm cells comprises: i) sorting the mesoderm cells to select for $KDR^+NCAM^+APLNR^+$ cells.

In various embodiments, the method includes one or more of the following further steps:

D. sorting the mesoderm cells to select for $SSEA5^-KDR^+NCAM^+APLNR^+$ cells;

E. culturing the cells undergoing mesodermal induction with Fc-NRP-1;

F. culturing the cells undergoing mesodermal induction with one or more miRNA inhibitor, one or more miRNA mimic, or a combination thereof;

G. inducing differentiation of the isolated mesoderm cells into cells of the endothelial lineage; and H. isolating ECFC-like cells from the differentiated cells of the endothelial lineage.

Each step in the aforementioned method is described further herein below.

A. Pluripotent Stem Cell Culture

In one aspect, a method for generating an isolated population of mesoderm and/or ECFC-like cells in vitro from pluripotent cells is provided. Pluripotent cells that are suitable for use in the methods of the present disclosure can be obtained from a variety of sources. For example, one type of suitable pluripotent cell is an embryonic stem (ES) cell derived from the inner cell mass of a blastocyst. Methods for obtaining various types of ES cells, such as mouse, rhesus monkey, common marmoset, and human, are well known. The source of ES cells used in the method may be, for example, one or more established ES cell lines. Various ES cell lines are known and the conditions for their growth and propagation have been defined. It is contemplated herein that virtually any ES cell or ES cell line may be used with the methods disclosed herein. In one embodiment, the pluripotent cell is an induced pluripotent stem (iPS) cell derived by reprogramming somatic cells. Induced pluripotent stem cells have been obtained by various known methods. It is contemplated herein that virtually any iPS cell or cell line may be used with the methods disclosed herein. In other embodiments, the pluripotent cell is an embryonic stem cell derived by somatic cell nuclear transfer, in which a donor nucleus is transferred into a spindle-free oocyte. Various methods for producing stem cells by nuclear transfer are known. It is contemplated herein that virtually any ES cells or cell line derived by somatic cell nuclear transfer may be used with the methods disclosed herein.

In one embodiment, pluripotent cells are cultured under conditions suitable for maintaining pluripotent cells in an undifferentiated state. Methods for maintaining pluripotent cells in vitro, i.e., in an undifferentiated state, are well known. In one embodiment, pluripotent cells are cultured for about two days under conditions suitable for maintaining pluripotent cells in an undifferentiated state. For example, in the Examples below, hES and hiPS cells were maintained in mTeSR1 complete medium on Matrigel™ in 10 cm² tissue culture dishes at 37° C. and 5% $CO_2$ for about two days.

Additional and/or alternative methods for culturing and/or maintaining pluripotent cells may be used. For example, as the basal culture medium, any of TeSR, mTeSR1 alpha.MEM, BME, BGJb, CMRL 1066, DMEM, Eagle MEM, Fischer's media, Glasgow MEM, Ham, IMDM, Improved MEM Zinc Option, Medium 199 and RPMI 1640, or combinations thereof, may be used for culturing and or maintaining pluripotent cells.

The pluripotent cell culture medium used may contain serum or it may be serum-free. Serum-free refers to a medium comprising no unprocessed or unpurified serum. Serum-free media can include purified blood-derived components or animal tissue-derived components, such as, for example, growth factors. The pluripotent cell medium used may contain one or more alternatives to serum, such as, for example, knockout Serum Replacement (KSR), chemically-defined lipid concentrated (Gibco) or glutamax (Gibco).

Methods for splitting or passaging pluripotent cells are well known. For example, in the Examples below, after pluripotent cells were plated, medium was changed on days 2, 3, and 4 and cells were passaged on day 5. Generally, once a culture container is full (i.e., 70-100% confluence), the cell mass in the container is split into aggregated cells or single cells by any method suitable for dissociation and the aggregated or single cells are transferred into new culture containers for passaging. Cell "passaging" or "splitting" is a well-known technique for keeping cells alive and growing cells in vitro for extended periods of time.

B. Directed Differentiation of Pluripotent Cells into Mesoderm Cells

In one aspect of the method disclosed, in vitro pluripotent cells are induced to undergo mesodermal differentiation, also referred to as a step of "mesodermal induction". Various methods, including culture conditions, for inducing differentiation of pluripotent cells into cells of the mesodermal lineage are known in the art. In the protocol provided herein it is preferable to induce differentiation of pluripotent cells in a chemically defined medium. For example, Stemline II serum-free hematopoietic expansion medium can be used as a basal mesodermal differentiation medium. In the protocol provided herein various growth factors are used to promote differentiation of pluripotent cells into cells of the mesodermal lineage. For example, Activin A, vascular endothelial growth factor (VEGF), basic fibroblast growth factor (FGF-2) and bone morphogenetic protein 4 (BMP-4) are included in a chemically defined differentiation medium to induce differentiation of pluripotent cells into cells of the mesodermal lineage.

In one embodiment of the protocol provided herein, after 2 days (−D2) of culture in a basal culture medium (e.g., mTeSR1), differentiation of pluripotent cells was directed toward the mesodermal lineage by contacting the cells for 24 hours with an endothelial differentiation medium comprising an effective amount of Activin A, BMP-4, VEGF and FGF-2. Following 24 hours of differentiation, Activin A was removed from the culture by replacing the mesodermal differentiation medium with an mesodermal differentiation medium comprising an effective amount of BMP-4, VEGF and FGF-2. By "effective amount", we mean an amount effective to promote differentiation of pluripotent cells into cells of the mesodermal lineage. Further replacement of the mesodermal differentiation medium comprising an effective amount of BMP-4, VEGF and FGF-2 may be done every 1-2 days for about 3 days (i.e., to D4).

Activin A is a member of the TGF-B superfamily that is known to activate cell differentiation via multiple pathways. Activin-A facilitates activation of mesodermal specification but is not critical for endothelial specification and subsequent endothelial amplification. In one embodiment, the mesodermal differentiation medium comprises Activin A in a concentration of about 5-25 ng/mL. In one preferred embodiment, the mesodermal differentiation medium comprises Activin A in a concentration of about 10 ng/mL.

Bone morphogenetic protein-4 (BMP-4) is a ventral mesoderm inducer that is expressed in adult human bone marrow (BM) and is involved in modulating proliferative and differentiative potential of hematopoietic progenitor cells. Additionally, BMP-4 can modulate early hematopoietic cell development in human fetal, neonatal, and adult hematopoietic progenitor cells. In one embodiment, the mesodermal differentiation medium comprises BMP-4 in a concentration of about 5-25 ng/mL. In one preferred embodiment, the mesodermal differentiation medium comprises BMP-4 in a concentration of about 10 ng/mL.

Vascular endothelial growth factor (VEGF) is a signaling protein involved in embryonic circulatory system formation and angiogenesis. In vitro, VEGF can stimulate endothelial cell mitogenesis and cell migration. In one embodiment, the mesodermal differentiation medium comprises VEGF in a concentration of about 5-50 ng/mL. In one preferred embodiment, the mesodermal differentiation medium comprises VEGF in a concentration of about 10 ng/mL. In one particularly preferred embodiment, the mesodermal differentiation medium comprises VEGF$_{165}$ in a concentration of about 10 ng/mL.

Basic fibroblast growth factor, also referred to as bFGF or FGF-2, has been implicated in diverse biological processes, including limb and nervous system development, wound healing, and tumor growth. bFGF has been used to support feeder-independent growth of human embryonic stem cells. In one embodiment, the mesodermal differentiation medium comprises FGF-2 in a concentration of about 5-25 ng/mL. In one preferred embodiment, the mesodermal differentiation medium comprises FGF-2 in a concentration of about 10 ng/mL.

The method disclosed herein does not require co-culture with supportive cells, such as, for example, OP9 stromal cells, does not require embryoid body (EB) formation and does not require exogenous TGF-β inhibition.

C. Isolating KDR$^+$NCAM$^+$APLNR$^+$ (KNA$^+$) Mesoderm Cells

In an aspect, KDR$^+$NCAM$^+$APLNR$^+$ cells are selected and isolated from the population of cells induced to undergo mesodermal differentiation. Methods, for selecting cells having one or more specific molecular markers are known in the art. For example, cells may be selected based on expression of various transcripts by flow cytometry, including fluorescence-activated cell sorting, or magnetic-activated cell sorting.

In one embodiment, KDR$^+$NCAM$^+$APLNR$^+$ cells are selected from a population of cells undergoing mesodermal differentiation, as described herein, on day 4 of differentiation. In one preferred embodiment, KDR$^+$ cells are selected from a population of cells undergoing mesodermal differentiation and then from the selected KDR$^+$ cells, NCAM$^+$APLNR$^+$ cells are selected, thereby yielding a population of KDR$^+$NCAM$^+$APLNR$^+$ cells.

In the Examples below, mesoderm cells were harvested after day 4 of differentiation and made into a single cell suspension. Cells were counted and prepared for antibody staining with anti-human antibodies to KDR, NCAM and APLNR. KDR$^+$NCAM$^+$APLNR$^+$ cells were gated/selected and sorted using flow cytometry.

The mesoderm subsets identified herein display gene products consistent with known subsets of human mesoderm. These specific mesoderm subsets have not previously been noted to give rise to human ECFCs.

In one embodiment, the selected cells have a capacity for in vivo vessel formation. This result was unexpected. Specific types of mesoderm are expressed in early human development, and those cells that give rise to angioblast cells (the first mesoderm-derived cells that further differentiate into endothelial cells) are predicted to be derived from extra-embryonic/lateral plate mesoderm. Accordingly, a skilled person would predict that mesoderm cells would differentiate at specific times in specific places to form the first blood vessels via vasculogenesis. A skilled person would not predict that mesoderm cells would display the ability to give rise to ECFCs and form human blood vessels in an adult immunodeficient mouse, at least because there are no mesoderm cells that exist in adult mice (they have already committed to lineage fates during embryogenesis and are now only represented by their specified lineage progeny).

D. Selection of SSEA5$^-$KDR$^+$NCAM$^+$APLNR$^+$ Cells

In one embodiment, SSEA5$^-$KDR$^+$NCAM$^+$APLNR$^+$ cells are selected from a population of cells undergoing mesodermal differentiation, as described herein, on day 4 of differentiation. In one preferred embodiment, SSEA5$^-$KDR$^+$ cells are selected from a population of cells undergoing mesodermal differentiation and then from the selected SSEA5$^-$KDR$^+$ cells, NCAM$^+$APLNR$^+$ cells are selected, thereby yielding a population of SSEA5$^-$KDR$^+$NCAM$^+$APLNR$^+$ cells.

The inventors found that negative selection of Day 4 differentiated cells with an SSEA5 antibody allowed identification and subsequent removal of an undifferentiated or partially differentiated hiPSCs mixture from day 4 differentiated cells. This was achieved by performing in vivo implantation of SSEA5$^-$KDR$^+$NCAM$^+$APLNR$^+$ cells and KDR$^+$NCAM$^+$APLNR$^+$ cells (without negative selection for SSEA5) in the same animal. One abdominal side received SSEA5$^-$KDR$^+$NCAM$^+$APLNR$^+$ cells and other abdominal side of the same animal received KDR$^+$NCAM$^+$APLNR$^+$ cells. Implanted KDR$^+$NCAM$^+$APLNR$^+$ cells formed blood vessels and endoderm derivatives, whereas implanted SSEA5$^-$KDR$^+$NCAM$^+$APLNR$^+$ cells formed blood vessels, and did not form endoderm and/or teratomas. Accordingly, one advantage of the SSEA5$^-$KDR$^+$NCAM$^+$APLNR$^+$ mesoderm cells provided herein is that they can be used to achieve selective ECFC blood vessel formation in vivo without formation of endodermal derivatives.

E. Mesodermal Induction with Fc-NRP-1

The inventors contemplated that stimulating KDR signalling in the cells undergoing mesoderm induction might increase mesoderm production. In one embodiment of the protocol provided herein, following 24 hours of differentiation in Activin-A containing medium, the mesodermal differentiation medium was replaced with a mesodermal differentiation medium comprising an effective amount of Fc-NRP-1, BMP-4, VEGF and FGF-2. By "effective amount", we mean an amount effective to promote differentiation of pluripotent cells into cells of the mesodermal lineage. Further replacement of the mesodermal differentiation medium comprising an effective amount of Fc-NRP-1, BMP-4, VEGF and FGF-2 may be done, for example, every 1-2 days for about 3 days (i.e., to D4). The inventors found that addition of Fc-NRP-1 to the mesoderm induction protocol improved mesoderm generation. This result is surprising, at least because NRP-1 (the Fc-NRP-1 acts as a surrogate for NRP-1) and VEGF$_{165}$ (the ligand that binds to Fc-NRP1 or endogenous NRP-1), are not expressed in the cells undergoing mesoderm induction. The other molecules that are known to activate KDR signaling are VEGF$_{165}$ and NRP-1. However, the inventors' studies show that neither of these molecules are endogenously expressed in the cells undergoing day 4 mesoderm differentiation. The inventors' identification of a soluble molecule (which could be used to supplement culture media) that can activate KDR signaling, thereby enhancing mesoderm formation, is advantageous for augmenting production of ECFC mesoderm cells.

F. Mesodermal Induction with miRNA Inhibitors and/or Mimics

In one embodiment of the protocol provided herein, cells being induced to undergo mesodermal differentiation are exposed to one or more miRNA inhibitors, mimics, or a combination thereof. The inventors have identified a set of miRNAs that are downregulated in SSEA5⁻KDR⁺NCAM⁺APLNR⁺ cells (miR-221-3p, miR-1271-5p, miR-559, miR-543, miR-361-3p, miR-30d-5p, miR-124-3p and miR-185-5p) and a set of miRNAs that were identified as being upregulated in SSEA5⁻KDR⁺NCAM⁺APLNR⁺ cells (miR-330-5p, miR-145-5p, miR-214-3p and miR-497-5p). The inventors have found that transfecting the cells undergoing mesoderm induction with one or more agents that mimic specific miRNAs that are upregulated in SSEA5⁻KDR⁺NCAM⁺APLNR⁺ cells increases the frequency of SSEA5⁻KDR⁺NCAM⁺APLNR⁺ cells generated from PSCs. The inventors have found that transfecting the cells undergoing mesoderm induction with one or more agents that inhibit specific miRNAs that were identified as being downregulated in SSEA5⁻KDR⁺NCAM⁺APLNR⁺ cells increases the frequency of SSEA5⁻KDR⁺NCAM⁺APLNR⁺ cells generated from PSCs. The inventors have also found that transfecting the cells undergoing mesoderm induction with a combination of specific miRNA mimics and inhibitors increases the frequency of SSEA5⁻KDR⁺NCAM⁺APLNR⁺ cells generated from PSCs.

In one embodiment of the protocol provided herein, after 2 days (−D2) of culture in a basal culture medium, differentiation of pluripotent cells was directed toward the mesodermal lineage by contacting the cells for 24 hours with an endothelial differentiation medium comprising an effective amount of Activin A, BMP-4, VEGF and FGF-2. During this first 24 hours (i.e., on D0), the cells were transfected with one of 4 treatments: i) 3 miRNA mimics; ii) 3 miRNA inhibitors; iii) 3 miRNA mimics and 3 miRNA inhibitors; or iv) a control. Following 24 hours of differentiation, Activin A was removed from the culture by replacing the mesodermal differentiation medium with an mesodermal differentiation medium comprising an effective amount of BMP-4, VEGF and FGF-2. The cells were transfected again, with the same treatment, on day 2 of mesodermal induction. Further replacement of the mesodermal differentiation medium comprising an effective amount of BMP-4, VEGF and FGF-2 may be done every 1-2 days for about 3 days (i.e., to D4). On day 4, cells were sorted and isolated, as described above.

G. Directed Differentiation of Isolated Mesoderm Cells into Cells of the Endothelial Lineage In one aspect of the method disclosed, the isolated mesoderm cells are induced to undergo endothelial differentiation. Various methods, including culture conditions, for inducing differentiation of mesoderm cells into cells of the endothelial lineage are known in the art. In the ECFC-like cell protocol provided herein it is preferable to induce differentiation of endothelial cells in a chemically defined medium. For example, Stemline II serum-free hematopoietic expansion medium can be used as a basal endothelial differentiation medium. In the ECFC-like cell protocol provided herein various growth factors are used to promote differentiation of pluripotent cells into cells of the endothelial lineage, including ECFC-like cells. For example, VEGF, FGF-2 and BMP-4 are included in a chemically defined differentiation medium to induce differentiation of isolated mesoderm cells into cells of the endothelial lineage, including ECFC-like cells.

In one embodiment of the ECFC-like cell protocol provided herein, isolated mesoderm cells are cultured with an endothelial differentiation medium comprising an effective amount of BMP-4, VEGF and FGF-2. By "effective amount", we mean an amount effective to promote differentiation of isolated mesoderm cells into cells of the endothelial lineage, including ECFC-like cells. Further replacement of the endothelial differentiation medium comprising an effective amount of BMP-4, VEGF and FGF-2 may be done every 1-2 days.

The method disclosed herein does not require co-culture with supportive cells, such as, for example, OP9 stromal cells, does not require embryoid body (EB) formation, and does not require exogenous TGF-β inhibition.

H. Isolating ECFC-Like Cells from the Differentiated Endothelial Cells

In one embodiment of the method disclosed herein, CD31+NRP-1+ cells are selected and isolated from the population of cells undergoing endothelial differentiation. For example, in one embodiment, CD31+NRP-1+ cells are selected from a population of cells undergoing endothelial differentiation, as described herein, on day 10, 11 or 12 of differentiation. In one preferred embodiment, CD31+NRP-1+ cells are selected from the population of cells undergoing endothelial differentiation on day 12 of differentiation. The inventors have found that the day 12 population of cells undergoing endothelial differentiation contains a higher percentage of NRP-1+ cells relative to cell populations that are present on other days of differentiation.

In the Examples below, adherent ECs were harvested after day 12 of differentiation and made into a single cell suspension. Cells were counted and prepared for antibody staining with anti-human CD31, CD144 and NRP-1. CD31+CD144+NRP-1+ cells were sorted and selected using flow cytometry.

In one embodiment, the selected cells exhibit a cobblestone morphology, which is typical of ECs, including ECFCs.

In one embodiment, the selected cells have a capacity for in vivo vessel formation in the absence of co-culture and/or co-implanted cells, which is typical of ECFCs.

III. Isolated Cell Populations

Isolated Mesoderm Cell Populations

In one embodiment, an isolated population of human KDR⁺NCAM⁺APLNR⁺ mesoderm cells is provided. In one embodiment, the purified human cell population of KDR⁺NCAM⁺APLNR⁺ mesoderm cells provided is generated using the in vitro method for generating mesoderm cells from hPSCs disclosed herein. The isolated KDR⁺NCAM⁺APLNR⁺ mesoderm cells of the population have a capacity to give rise to ECFCs and the capacity for blood vessel formation in vivo. In one embodiment, the KDR⁺NCAM⁺APLNR⁺ mesoderm cells of the population are further characterized by increased expression of one or more lateral plate-extra-embryonic mesoderm markers (e.g., BMP4, WNT5A, NKX2-5 and/or HAND1) relative to PSCs. In one embodiment, the KDR⁺NCAM⁺APLNR⁺ mesoderm cells of the population are further characterized by a lack of increased expression of one or more axial mesoderm markers (e.g., CHIRD and/or SHH), paraxial mesoderm markers (e.g., PAX1, MEOX1, and TCF15) and/or intermediate mesoderm markers (e.g., GOSR1, PAX2 and PAX8), relative to PSCs.

In one embodiment, an isolated population of human SSEA5⁻KDR⁺NCAM⁺APLNR⁺ mesoderm cells is provided. In one embodiment, the purified human cell population of SSEA5⁻KDR⁺NCAM⁺APLNR⁺ mesoderm cells provided is generated using the in vitro method for generating mesoderm cells from hPSCs disclosed herein. The isolated SSEA5⁻KDR⁺NCAM⁺APLNR⁺ mesoderm cells of the population have a capacity for ECFC formation and blood vessel formation in vivo. In one embodiment, the SSEA5⁻KDR⁺NCAM⁺APLNR⁺ mesoderm cells of the population are further characterized by increased expression of one or more lateral plate-extra-embryonic mesoderm markers (e.g., BMP4, WNT5A, NKX2-5 and/or HAND1) relative to PSCs. In one embodiment, the SSEA5⁻KDR⁺NCAM⁺APLNR⁺ mesoderm cells of the population are further characterized by a lack of increased expression of one or more axial mesoderm markers (e.g., CHIRD and/or SHH), paraxial mesoderm markers (e.g., PAX1, MEOX1, and TCF15) and/or intermediate mesoderm markers (e.g., GOSR1, PAX2 and PAX8), relative to PSCs.

In one preferred embodiment, the isolated mesoderm cell population is substantially pure. In one embodiment, 28% of total live cells at day 4 of mesoderm differentiation are KDR⁺NCAM⁺APLNR⁺. In one embodiment, 18% of total live cells at day 4 of mesoderm differentiation are SSEA5⁻KDR⁺NCAM⁺APLNR⁺.

Isolated ECFC-Like Cell Populations

In one embodiment, an isolated population of human NRP-1⁺/CD31⁺ ECFC-like cells is provided. In one embodiment, the purified human cell population of NRP-1⁺/CD31⁺ ECFC-like cells provided is generated using the in vitro method for generating ECFC-like cells from hPSCs disclosed herein.

In the Examples below, the method disclosed herein is used to generate a purified human cell population of NRP-1+ and CD31+ ECFC-like cells, from an isolated subset of mesoderm cells. The isolated ECFC-like cells of the population exhibit cobblestone morphology and have a capacity for blood vessel formation in vivo without co-culture and/or co-implanted cells. In one embodiment, the ECFC-like cells of the population are further characterized by one or more of CD144+, KDR+ and α-SMA−.

In one embodiment, at least some of the ECFC-like cells in the population generated from the isolated mesoderm cells have a high proliferation potential that is similar to the proliferation potential of ECFC's generated in vitro using the inventor's previous hPSC-ECFC-lice cell protocol.

In one preferred embodiment, the isolated ECFC-like cell population is substantially pure.

In the Examples herein, cells in the ECFC-like cell populations generated from the disclosed mesoderm cells can form blood vessels when implanted in vivo in a mammal, even in the absence of supportive cells.

Various techniques for measuring in vivo vessel formation are known and can be used.

The capacity to form blood vessels in vivo in the absence of exogenous supportive cells is one indicator that the cells produced using the methods disclosed herein are ECFCs.

IV. Use of Mesoderm and/or ECFC-like Cells Disclosed Herein

In contrast to known mesoderm cell lines and other known isolated mesoderm cells described previously, the mesoderm cells generated using the method disclosed herein can be generated in vitro and used to form blood vessel tissue in vivo for various clinical applications, as described below.

In contrast to ECFCs, which are primary cells, the ECFC-like cells generated using the method disclosed herein can be generated in vitro in a volume that can be useful for various clinical applications, as described below.

A. Therapy

In one aspect, methods, cells and compositions suitable for cell transplantation, cell replenishment, and/or cell or tissue replacement are provided herein. The method can comprise providing to a subject in need thereof a therapeutically effective amount of mesoderm and/or ECFC-like cells derived according to a method provided herein, whereby providing mesoderm and/or ECFC-like cells treats the subject. By "therapeutically effective amount", we mean an amount effective to treat a subject who is in need of epithelial repair. In a preferred embodiment, the epithelial repair is vascular epithelial repair The cells and/or compositions provided herein may be administered to a subject in a manner that permits the mesoderm and/or ECFC-like cells to graft or migrate to an intended tissue site and reconstitute or regenerate the functionally deficient area, such as, for example, a blood vessel.

Subjects suitable for receiving therapy using the mesoderm and/or ECFC-like cells provided herein include those having endothelial dysfunction and/or damage of various kinds. For example, subjects having cardiovascular disease, myocardial infarction, cardiac stroke, or peripheral artery disease (PAD) can be suitable subjects for receiving therapy using the mesoderm and/or ECFC-like cells of the present disclosure. Subjects having lung or kidney disease or damage can be suitable subjects for receiving therapy using the mesoderm and/or ECFC-like cells of the present disclosure. In preferred embodiments, PAD patients developing critical limb ischemia (CLI) can be suitable subjects for receiving therapy using the mesoderm and/or ECFC-like cells of the present disclosure.

In one embodiment, the mesoderm and/or ECFC-like cells can be provided to a subject in the form of a pharmaceutical composition suitable for human administration. For example, the composition may comprise one or more pharmaceutically acceptable carriers, buffers, or excipients. The composition may further comprise, or be provided to the subject with, one or more ingredients that facilitate the engraftment mesoderm and/or ECFC-like cells. For example, the pharmaceutical composition may also comprise, or be provided to a subject with, one or more growth factors or cytokines (e.g., angiogenic cytokines) that promote survival and/or engraftment of transplanted cells, promote angiogenesis, modulate the composition of extracellular or interstitial matrix, and/or recruit other cell types to the site of transplantation.

In one embodiment, the pharmaceutical composition may be formulated, produced, and stored according to standard methods that provide proper sterility and stability.

For example, in one embodiment, the mesoderm and/or ECFC-like cells provided herein may be directly injected into a tissue that is lacking in adequate blood flow (as determined by a physician). In one embodiment, the mesoderm and/or ECFC-like cells provided herein may be suspended in a matrix comprised of collagen, fibronectin, or a synthetic material and this gelatinous suspension of the mesoderm and/or ECFC-like cells may be directly injected into a tissue that is lacking in adequate blood flow. The concentration of mesoderm and/or ECFC-like cells injected into the tissue may vary, for example, from about 10,000 to about 100,000 cells/microliter of delivery vehicle or matrix material. In some tissues, the cells may be delivered on a single occasion with recovery of adequate blood flow whereas other tissues may require multiple injections and sequential injections over time to rescue adequate blood flow.

After administering the mesoderm and/or ECFC-like cells into the subject, the effect of the treatment method may be evaluated, if desired and the treatment may be repeated as needed or required. Therapy efficacy can be monitored by clinically accepted criteria known in the art, such as, for example, reduction in area occupied by scar tissue, revascularization of scar tissue, frequency and severity of angina; an improvement in developed pressure, systolic pressure, end diastolic pressure, subject mobility and/or quality of life.

ECFC cells can rescue an eye from hypoxia and neovascularization. Therefore, it is contemplated herein that the mesoderm and/or ECFC-like cells provided herein be used to treat various eye diseases in which hypoxia and neovascularization occurs, such as, for example, retinopathy of prematurity, diabetic retinopathy, central vein occlusion, or macular degeneration.

It is also contemplated that the mesoderm and/or ECFC-like cells provided herein may be used to coat at least a portion of the inside of a vascular stent and optionally any area of a vessel that became denuded of endothelial cells during the stent placement. In this case, the intravenously injected mesoderm and/or ECFC-like cells would bind to areas of injury and re-endothelialize the vessels to prevent blood clot formation and/or restenosis of the vessel area in which the stent has been placed.

It is known that placement of human veins (saphenous or umbilical) as grafts into arteries of patients that have areas of stenosis and blockade of blood flow, have a high incidence of subsequent stenosis and blocked blood flow. This is associated with loss of the blood vessel endothelial cells early in the process of vessel remodeling in vivo. It is contemplated herein that the mesoderm and/or ECFC-like cells provided herein can be intravenously injected into the vasculature of such a patient in order to re-endothelialize the implanted graft and to preserve the function of the vessel in the patient.

B. Test Agent Screening

The mesoderm and/or ECFC-like cells disclosed herein can be used to screen for factors (such as solvents, small molecule drugs, peptides, oligonucleotides) or environmental conditions (such as culture conditions or manipulation) that affect the characteristics of mesoderm and/or ECFC-like cells and any tissues developed therefrom. In one embodiment, test agents, such as, for example, pharmaceutical compounds, can be screened using the mesoderm and/or ECFC-like cells of the present disclosure to determine their effect on endothelial health and/or repair. For example, screening may be done either because the compound is designed to have a pharmacological effect on the endothelial cells, or because a compound designed to have effects elsewhere may have unintended side effects on endothelial cells. In various embodiments, the mesoderm and/or ECFC-like cells herein are particularly useful for test agent screening, at least because they are differentiated in vitro from cultured pluripotent cells. In contrast, CB-ECFCs are primary cells obtained from patient blood and previously known isolated mesoderm cells do not have in vivo blood vessel-forming capacity. Various methods of screening test agent compounds are known in the art and can be used with the mesoderm and/or ECFC-like cells disclosed herein.

For example, screening the activity of test agents may comprise: i) combining the mesoderm and/or ECFC-like cells disclosed herein with a test agent, either alone or in combination with other agents; ii) determining changes in the morphology, molecular phenotype, and/or functional activity of the mesoderm and/or ECFC-like cells that can be attributed to the test agent, relative to untreated cells or cells treated with a control agent; and iii) correlating the effect of the test agent with the observed change.

In one embodiment, cytotoxicity of a test agent on the mesoderm and/or ECFC-like cells provided herein can be determined by the effect the agent has on one or more of mesoderm and/or ECFC-like cell viability, survival, morphology, and molecular phenotype and/or receptors.

In one embodiment, mesoderm and/or ECFC-like cell function can be assessed using a standard assay to observe phenotype or activity of the mesoderm and/or ECFC-like cells. For example, one or more of molecular expression, receptor binding, either in cell culture or in vivo, may be assessed using the mesoderm and/or ECFC-like cells disclosed herein.

C. Kits

In one embodiment, kits for use with methods and cells disclosed herein are contemplated. In one embodiment, a kit can comprise a differentiation and/or growth medium, as described herein, in one or more sealed vials. In one embodiment, the kit can include one or more cells, such as pluripotent cells, mesoderm cells and/or ECFC-like cells, as disclosed herein. In one embodiment, the kit can include one or more miRNA mimic, one or more miRNA inhibitor, or a combination thereof. In one embodiment, the kit can include Fc-NRP-1. In one embodiment, the kit can include instructions for generating mesoderm cells from pluripotent cells. In one embodiment, the kit can include instructions for generating ECFC-like cells from pluripotent cells. In one embodiment, kits can include various reagents for use with the present disclosure in suitable containers and packaging materials. In one embodiment, the kit can include one or more controls for use with the present disclosure in suitable containers and packaging materials.

The disclosure will be more fully understood upon consideration of the following non-limiting Examples.

EXAMPLES

Example 1: Materials and Methods

Culturing of hPSCs: Human Embryonic stem cell (hES) cell line H9 (Thomson et al., 1998 Science; 282:1145-1147) and fibroblast-derived human iPS cell line (DF19-9-11T) (Yu et al. 2009 Science 324:797-801) were purchased from WiCell Research institute (Madison, Wis.). Both hES and hiPSCs were maintained in mTeSR1 complete media (Stem Cell Technologies) on Matrigel in 10 cm$^2$ tissue culture dishes at 37° C. and 5% $CO_2$. After the plating of cells, media was changed on days 2, 3, and 4. Cells were passaged on Day 5. Media was aspirated and 4-5 mL of dispase (2 mg/mL, Gibco) containing media was added to the plate and incubated at 37° C. for 3-5 minutes or until the edges of the colonies had lifted from the plate. Dispase containing media was aspirated from the plate and cells were gently washed with DMEM-F12 (Gibco) 3 times to remove any residual amount of enzyme. Fresh media was then used to collect colonies from the plate using a forceful wash and scraping with a 5 mL disposable pipette taking care to avoid bubbles. Collected colonies were then centrifuged at 300× g for 5 minutes. The supernatant was aspirated and pellet was resuspended in mTeSR1 complete media. Prior to passaging, 10 cm² tissue culture dishes were coated with Matrigel for 30 minutes. Unattached Matrigel was removed from the tissue culture dishes and 7 mL of mTeSR1 complete medium was added to dishes. Colonies evenly distributed in mTeSR1 media were added to each plate. Cells were then spread out within the dish using multiple side to side shaking motions while avoiding any swirling. Cultures were checked for growth quality and morphology, and by performing teratoma formation assay as previously described (Broxmeyer et al., 2011 Blood; 117:4773-4777).

Directed differentiation of hPSCs into mesoderm cells: After 2 days (−D2) of culture in mTeSR1 media, cultures were directed toward the mesodermal lineage with addition of activin A (10 ng/mL) in the presence of FGF-2, $VEGF_{165}$, and BMP4 (10 ng/mL) for 24 hrs. The following day (D1), activin-A containing media was removed and replaced with 8 mL of Stemline II complete media (Sigma) containing FGF-2 (Stemgent), $VEGF_{165}$ (R&D) and BMP4 (R&D). Media was replaced with 8 ml of fresh Stemline II differentiation media on day 3. On day 4 the cells were collected for sorting by flow cytometry for KNA+ mesoderm cells or SSEA5-KNA+ mesoderm cells.

Directed differentiation of KNA+ mesoderm cells or SSEA5-KNA+ mesoderm cells into the EC lineage, including ECFC-like cells: Day 4 sorted mesoderm cells ($KDR^+NCAM^+APLNR^+$ or $SSEA5^-KDR^+NCAM^+APLNR^+$) were further cultured with 8 mL of Stemline II complete media (Sigma) containing FGF-2 (Stemgent), $VEGF_{165}$ (R&D) and BMP4 (R&D), which was replaced on days 6, 8, 10 and 12. On day 10 and thereafter media was changed with 10 mL of Stemline II differentiation media.

Flow cytometry: At day 12 after differentiation, adherent cells were harvested using TrypleE and made into a single cell suspension in EGM-2 medium. Cells were counted and aliquots of the cell suspension were prepared for antibody staining. FcR blocking reagent (Miltyni Biotech) was added to prevent the non-specific binding of antibodies. Anti-human CD31 (CD31-FITC, clone WM59 from BD Pharmingen), CD144 (CD144-PE, clone 16B1 from ebioscience) and NRP-1 (NRP-1-APC, clone AD5-176 from Miltenyi Biotech) antibodies were used at concentrations that were titrated prior to use. Propidium Iodide (PI, Sigma) was added to the cell suspension for dead cell staining. Flow cytometric detection of the cell surface antigens and cells sorting were performed on an LSR II and FACS Aria (Becton Dickinson) respectively. Compensation was set by single positive controls using cord blood derived ECFCs. A gating of targeted cell population was determined based on fluorescent minus one (FMO) controls for each fluorescent color.

Cell culture of sorted cells: $CD31^+$, $CD144^+$ or $KDR^+$ and $NRP-1^+$ sorted cells were centrifuged at 300× g for 5 minutes then resuspended in 50% EGM-2 and 50% complete Stemline II differentiation media. To generate ECFCs from the sorted population, 2500 cells per well were seeded on rat tail type I collagen coated 12 well plates. After 2 days, the media was aspirated and three parts of EGM-2 and one part of differentiation media was added to the cultures. ECFC colonies appeared as tightly adherent cells and exhibited cobblestone morphology on day 7. On occasion, cloning cylinders were used to isolate ECFC colonies from heterogeneous cell populations. Cloning of endothelial cell clusters was performed to isolate pure populations of highly proliferative endothelial cells as described previously (Yoder et al., 2007; Ingram et al., 2005). Confluent ECFCS were passage by plating 10,000 cells per cm² as a seeding density and maintain ECFCs in complete endothelial growth media (collagen coated plates and cEGM-2 media) with media change every other day as described previously (Yoder et al., 2007; Ingram et al., 2005).

Immunochemistry: ECFCs were fixed with 4% (w/v) paraformaldehyde for 30 minutes and permeabilized with 0.1% (v/v) TritonX-100 in PBS for 5 minutes. After blocking with 10% (v/v) goat serum for 30 min, cells were incubated with primary following antibodies; anti-CD31 (Santa Cruz), anti-CD144 (ebioscience), anti-NRP-1 (Santa Cruz) and anti-a-SMA, (Chemicon) overnight at 4° C. Cells were washed with PBS, then incubated with secondary antibodies conjugated with Alexa-488 or Alexa-565 (Molecular Probe) and visualized by confocal microscopy after counterstaining with 2 g/ml DAPI (Sigma-Aldrich). The confocal images were obtained with an Olympus FV1000 mpE confocal microscope using as an Olympus uplanSApo 60×W/1.2NA/eus objective. All the images were taken as Z-stacks with individual 10μ thick sections at room temperature and images were analyzed using FV10-ASW 3.0 Viewer.

Mice: All animal procedures were carried in accordance with the Guidelines for the Care and Use of Laboratory Animals and were approved by the Institutional Animal Care and Use Committees (IACUCs) at Indiana University School of Medicine (IACUC protocol #10850). Both male and female 6-12 week old NOD/SCID mice (T- and B-cell deficient, impaired complement) were used for all animal studies. NOD-SCID mice were maintained under specific-pathogen-free conditions at the Indiana University Laboratory Animal Resource Center (LARC). Previous work with this animal model was used to determine the minimum number of animals needed to obtain statistically significant results (Yoder et al., 2007). Previous studies have shown that 8 out of 10 matrices (one animal received two matrices) implanted inosculate with the host vasculature and that 8 matrices (4 animals) with functional vessels are needed for each group for statistical significance (Yoder et al., 2007). Method of randomization was not used while allocating samples and animals to each experimental group. Also, investigator was not blinded to the group allocation both during the experiment and when accessing the outcomes.

In vivo implantation/vessel formation assay (including functional assay): Pig skin type I collagen was used to generate three-dimensional (3D) cellularized collagen matrices as previously described (Critser et al., 2010). Briefly, type 1 collagen gel mixture was prepared by mixing together ice-cold porcine skin collagen solution, 10% v/v human platelet lysate in 0.01N HCL, and neutralized with phosphate buffered saline and 0.1N NaOH to achieve neutral pH (7.4). Neutralized gel mixtures (~1.5 mg/mL) were kept on ice before induction of polymerization by warming at 37° C., in 5% $CO_2$. KNA+ mesoderm cells or SSEA-KNA+ mesoderm cells or SSEA-KNA+-derived NRP-1+CD31+ ECFCs were added to the collagen mixture to a final concentration of four million cells/ml collagen. The collagen mixture (250 μL) containing the cell suspension was added to 48-well tissue culture dishes and was allowed to polymerize to form gels by incubation in a $CO_2$ incubator at 37° C. for 30 minutes. The gels were then overlaid with 500 μl of culture medium for 30 min at 37° C., in 5% $CO_2$. After 1 hour of ex vivo 3D culture, cellularized gels were implanted into the flanks (a bluntly dissected subcutaneous pouch of anterior abdominal wall with close proximity of host vasculature) of 6- to 12-week-old NOD/SCID mice as previously described {Yoder, 2007 #71}. Surgical procedures to implant collagen gels were conducted under anesthesia and constant supply of oxygen. Incisions were sutured and mice monitored for recovery. Various days after implantation, gels were recovered by excising engrafts in animals that had been humanely sacrificed per approved IACUC protocol. Confocal fluoresce imaging and immunohistochemistry was performed as described previously using H&E and anti-human CD31 (and NRP-1) staining to examine the gels for human endothelial-lined vessels perfused with mouse red blood cells. hCD31$^+$ blood vessels were imaged from each explant using a Leica DM 4000B microscope (Leica Microsystems) with attached Spot-KE digital camera (Diagnostic Instruments). Functional vessels were counted only if they contained at least 1 mouse erythrocyte. Olympus-FV-1000 MPE inverted confocal/2P system us utilized to examine NRP-1$^+$ CD31$^+$ vessels.

Gene and miRNA expression analysis: Reverse transcriptase (RT) reactions were performed in a GeneAmp PCR 9700 Thermocycler (Applied Biosystems). mRNA RT reactions were performed using Transcriptor Universal cDNA Master (Roche). Specific miRNA primers were used for specific miRNA of interest for generating cDNA. RT reactions without templates or primer were used as controls. Gene and miRNA expression levels were quantified using the ABI 7300 RT-PCR System (Applied Biosystems). Quantitative PCR for mRNA was performed using FastStart Universal SYBR green master (Rox) (Roche). Comparative real-time PCR with or without specific primers for miRNAs and mRNAs was performed in triplicates. mRNA reactions were performed at 95° C. for 10 min, followed by 40 cycles of 95° C. for 15 s and 60° C. for 1 min. miRNA reactions were performed by 40 cycles of 95° C. for 15 s and 60° C. for 1 min. Relative expression levels were calculated using the comparative Ct method (Lee et al., 2013).

ECFC single cell proliferation assays: KNA+ or SSEA5-KNA+ mesoderm cell-derived ECFCs were subjected to a single cell assay to evaluate clonogenic proliferative potential. Briefly, endothelial cells were treated with trypLE Express (Invitrogen) to obtain a single cell suspension. Cell counts and serial dilutions were performed to obtain a concentration of 0.68 cells per well in individual wells of 96-well culture plates. Wells were examined the day after plating to ensure the presence of a single cell per well. Culture media was changed on days 4, 8, and 12. On day 14 of culture, cells were stained with Sytox reagent (Invitrogen), and each well was examined to quantitate the number of cells using a fluorescent microscope. Those wells containing two or more cells were identified as positive for proliferation under a fluorescent microscope at 10× magnification using a Zeiss Axiovert 25 CFL inverted microscope with a 10× CP-ACHROMAT/0.12 NA objective. Wells with endothelial cell counts of 2-50, 51-500, 501-2000 and 2001 were labeled as endothelial cell clusters (ECCs), low proliferative potential ECFCs (LPP) and high proliferative potential ECFCs (HPP) as previously described (Yoder et al., 2007; Ingram et al., 2005).

Western blot analysis: Cell lysates were prepared by resuspending cells in lysis buffer (20 mM Tris-HCl pH 7.5, 150 mM NaCl, 10% glycerol, 1% Triton X-100, 2 mM EDTA, 1 mM Na$_3$VO$_4$, 1 µg/ml each of aprotinin and leupeptin) followed by incubation on ice for 20 min. Insoluble components were removed by centrifugation at 12,000× g for 15 min. Protein concentrations were determined with a protein assay kit (Bio-rad). Proteins were separated by electrophoresis on 4-20% Tris-glycine minigels and then transferred onto immobilon-FL PVDF membrane (Millipore). Nonspecific binding was blocked with blocking buffer for 1 hr at room temperature and incubated overnight at 4° C. with primary antibodies against phospho-PYK2 (1:1,000; Cell Signaling) and phospho-p130$^{cas}$ (1:1,000; Cell Signaling) in Odyssey blocking buffer. Blots were washed with PBS containing 0.1% Tween20, followed by incubation for 1 hour at room temperature with anti-rabbit antibody (1:10,000; LI-COR). Immunoreactive bands were detected using the Odyssey Infrared Imager (LI-COR).

Fc-NRP-1 treatment assay: After 2 days (−D2) of culture of hiPSC clumps in mTeSR1 media, cultures were directed toward the mesodermal lineage with addition of activin A (10 ng/mL) in the presence of FGF-2, VEGF$_{165}$, and BMP4 (10 ng/mL) for 24 hrs. The following day (D1), activin-A containing media was removed and replaced with 8 mL of Stemline II complete media (Sigma) containing FGF-2 (Stemgent), VEGF$_{165}$ (R&D) and BMP4 (R&D) and 500 ng/mL of Fc-NRP-1 (R&D). Media was replaced with 8 ml of fresh Stemline II differentiation media containing FGF-2 (Stemgent), VEGF$_{165}$ (R&D) and BMP4 (R&D) and 500 ng/mL of Fc-NRP-1 (R&D) on day 3. On day 4 the cells were collected for sorting by flow cytometry for SSEA5-KNA+ mesoderm cells.

miRNA microarray and RNA sequence analysis: Total RNA was isolated from the samples using Trizol reagent (Invitrogen) and the RNA quality was examined as previously described (Ginsberg et al., 2012, Cell 151:559-575). For miRNA microarray, miRNome miRNA PCR Array plates, miScript II Reverse Transcription reaction kits, and miScript SYBR Green PCR Kits (all from Qiagen) were used to examine the expression profiles of the 1008 most abundantly expressed and best characterized miRNA sequences in the human miRNA genome (miRNome) as annotated in miRBase Release 16. For, RNA-seq analysis, RNA sequence library was generated using 1 µg of high quality total RNA and sequencing was performed using Illumina HiSeq2000 sequencer as previously described (Ginsberg et al., 2012). The resulting sequence reads were mapped to the human genome (hg18) using TopHat with default parameters, and the RefSeq (June 2010) transcript levels (FPKMs) were quantified using CuffLinks.

miRNA mimic/inhibitor treatment assay: After 1 day (−D1) of culture of single cell suspension of hiPSCs in mTeSR1 media, cultures were directed toward the mesodermal lineage with addition of activin A (10 ng/mL) in the presence of FGF-2, VEGF$_{165}$, and BMP4 (10 ng/mL) and 2.5 µg mimic or inhibitor/100,000 seeded cells/well of 6 well plate (GE Dharacon) for 24 hrs. The following day (D1), activin-A and miRNA mimic or inhibitor containing media was removed and replaced with 2 mL of Stemline II complete media (Sigma) containing FGF-2 (Stemgent), VEGF$_{165}$ (R&D) and BMP4 (R&D). Media was replaced with 2 ml of fresh Stemline II differentiation media containing FGF-2 (Stemgent), VEGF$_{165}$ (R&D) and BMP4 (R&D) and 2.5 µg mimic or inhibitor on day 2. Media was replaced with 2 ml of fresh Stemline II differentiation media containing FGF-2 (Stemgent), VEGF$_{165}$ (R&D) and BMP4 (R&D) on day 3. On day 4 the cells were collected for sorting by flow cytometry for SSEA5-KNA+ mesoderm cells.

Statistical analysis: All experiments were performed times in triplicate and data are represented as mean value±SD for statistical comparison. A power of analysis with a 95% confidence interval was used to calculate sample size required to obtain statistically significant results. The sampling number we used gave a normal distribution. Significance of differences was assessed by a two tailed student's t-test or one way ANOVA-Tukey post-hoc test Multiple Comparison Test.

Example 2

Referring now to FIGS. 1A-1G, NCAM and APLNR co-expressing cells within day 4 (D4) KDR$^+$ mesoderm cells (KNA$^+$ mesoderm) gave rise to NRP-1$^+$CD31$^+$ endothelial cells with ECFC competence.

Human PSCs cultured in mTeSR1 were induced to differentiate into mesoderm cells under 2D, serum and feeder-free conditions. PSCs were cultured in Stemline-II medium with FGF-2 (10 ng/mL), BMP4 (20 ng/mL), VEGF165 (10 ng/mL) and Activin-A (10 ng/mL) for 24 hours (i.e., from D0-D1) (FIG. 1A). On D1, the cell culture medium was replaced with Stemline-II medium with FGF-2 (10 ng/mL), BMP4 (20 ng/mL), VEGF$_{165}$ (10 ng/mL). This replacement medium was used to culture the cells undergoing mesodermal induction for 3 days (i.e., from D1-D4).

Figure 1B:
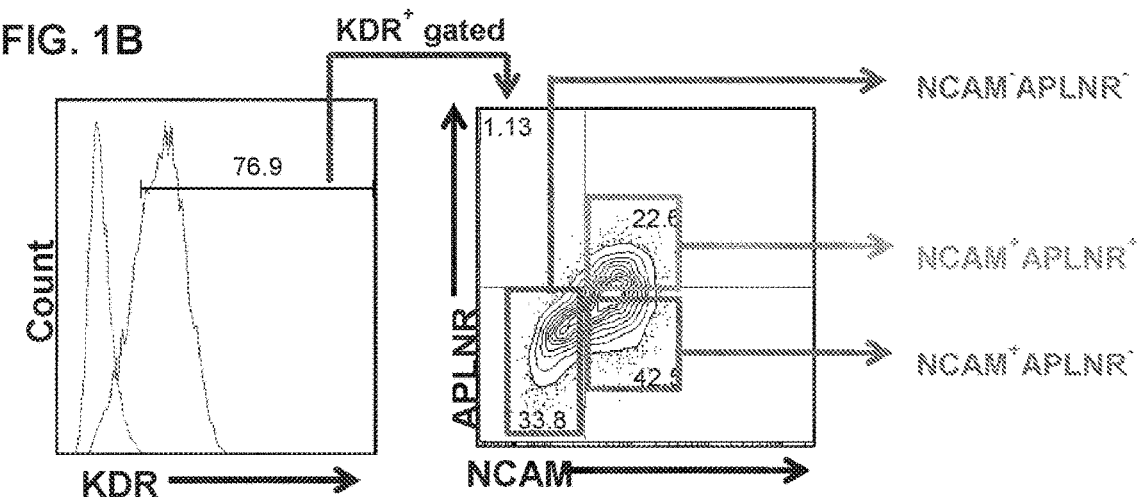
Figure 1C:
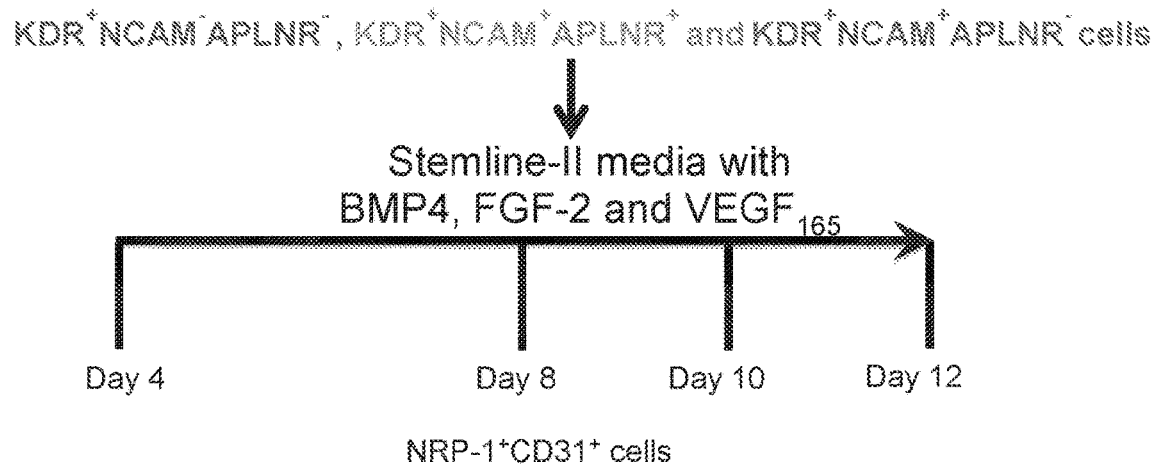
Figure 1D:
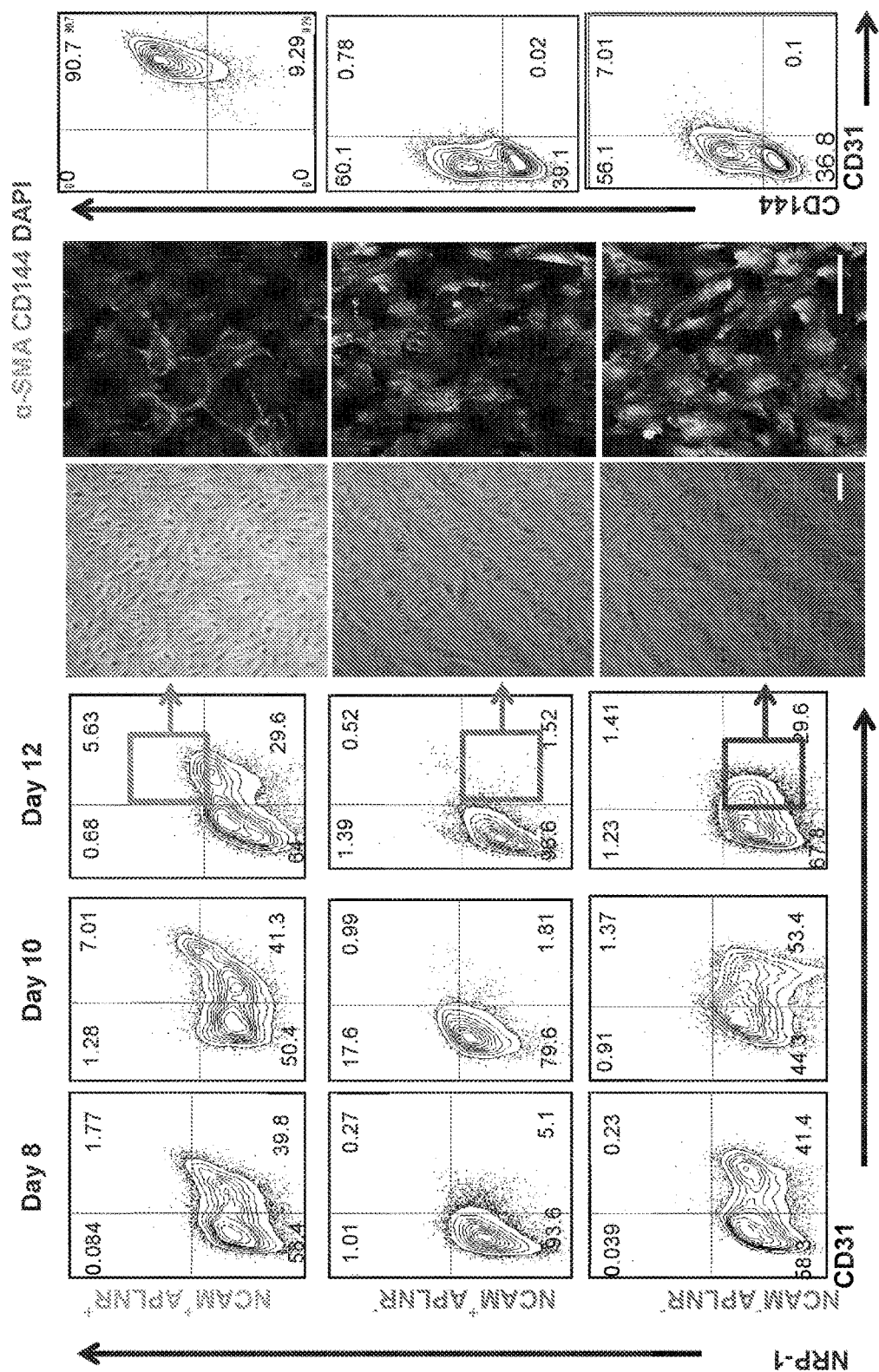
Figure 1E:
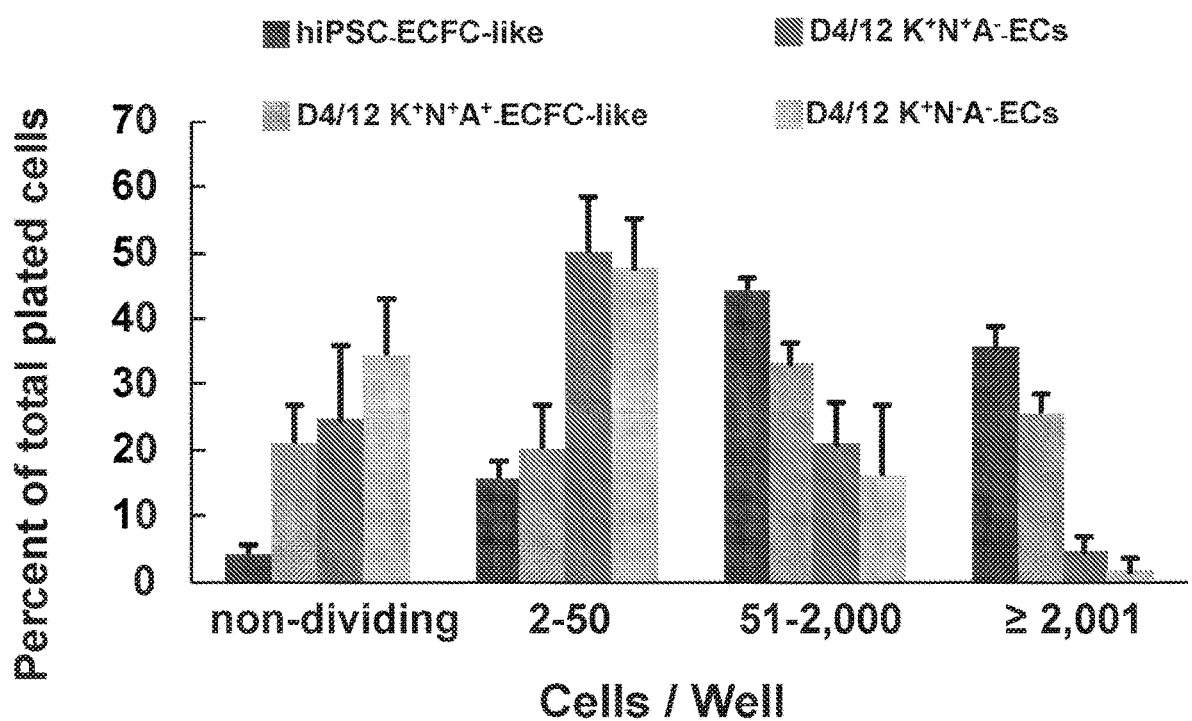
Figure 1F:
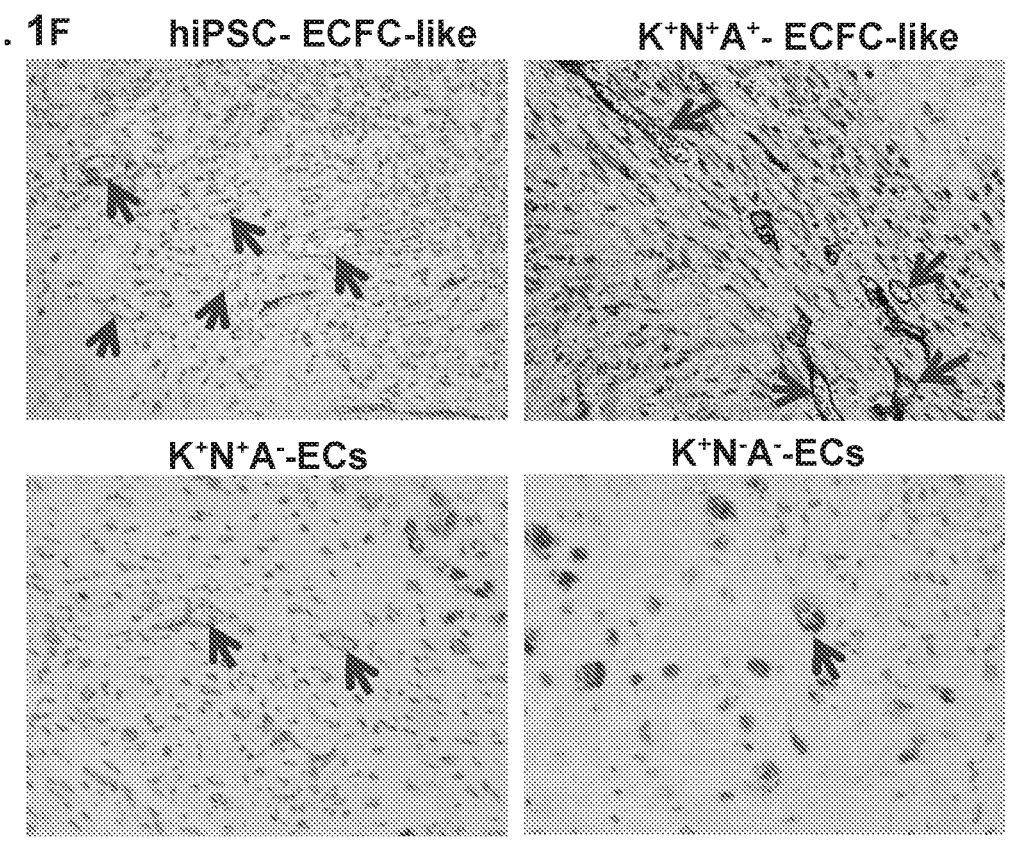
Figure 1G:
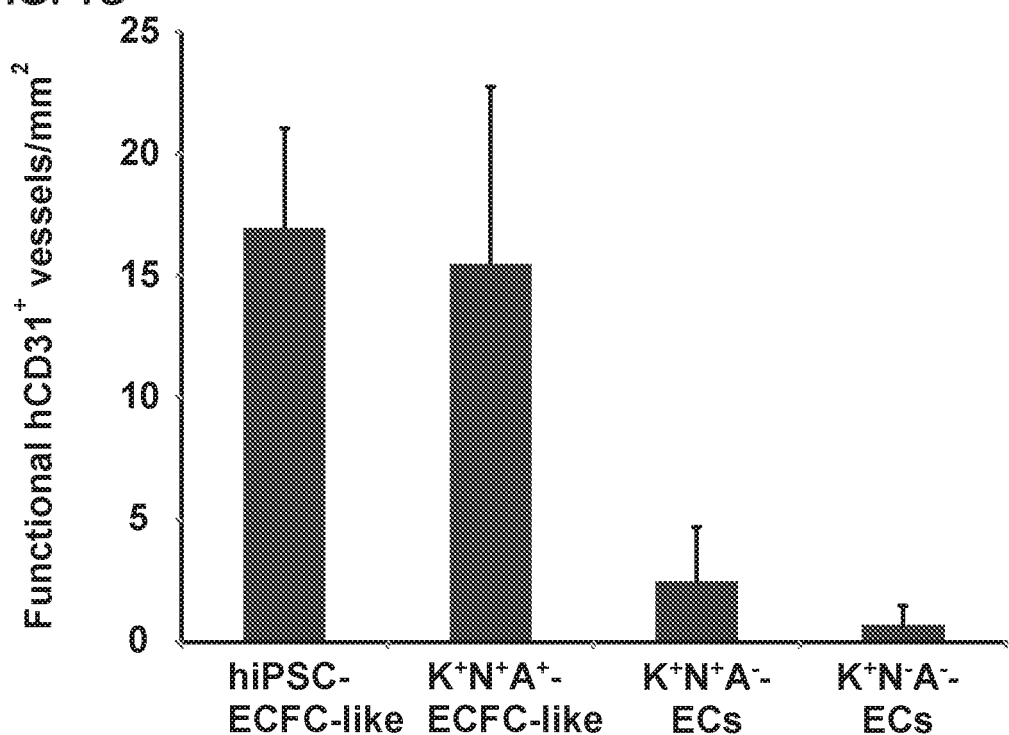

On Day 4, the cells induced to differentiate into mesoderm cells were sorted (FIG. 1B). KDR$^+$ cells were gated for NCAM and APLNR expression. KDR$^+$NCAM$^+$APLNR$^+$ (K$^+$N$^+$A$^+$, also referred to herein as KNA$^+$) and KDR$^+$NCAM$^+$APLNR$^-$ (K$^+$N$^+$A$^-$) KDR$^+$NCAM$^-$APLNR$^-$ (K$^+$N$^-$A$^-$) cells were sorted for further differentiation and examination for the emergence of NRP-1$^+$CD31$^+$ ECFC-like cells (FIG. 1O). Sorted K$^+$N$^+$A$^+$, K$^+$N$^+$A$^-$ and K$^+$N$^-$A$^-$ mesoderm sub-sets that were further differentiated into ECFC lineage for another 9 days (3 plus 9, total of 12 days) to examine for the emergence of NRP-1$^+$CD31$^+$ cells at various days of differentiation (FIG. 1D). At day 12, the K$^+$N$^+$A$^+$ mesoderm fraction gave rise to NRP1$^+$CD31$^+$ cells that formed a homogenous cobblestone endothelial monolayer, displayed uniform co-expression for CD31 and CD144 endothelial markers and completely lacked α-SMA expression (top panels of FIG. 1D), suggesting a stable ECFC-like phenotype. However, cells isolated from the other two subsets (i.e., K$^+$N$^+$A$^-$ (center panels of FIG. 1D) and K$^+$N$^-$A$^-$ (lower panels of FIG. 1D)) lacked adequate NRP-1 expression, formed heterogeneous cell monolayers, displayed expression for CD144 but lacked uniform co-expression for CD31 and CD144 endothelial markers and exhibited expression for the non-endothelial marker α-SMA, suggesting a complete lack of a stable ECFC phenotype. The K$^+$N$^+$A$^+$ mesoderm-derived NRP-1$^+$CD31$^+$ cells exhibited high clonal proliferative potential with a hierarchy of colonies ranging from clusters of 2-50 cells up to colonies of >2001 similar to that of hiPSC-ECFC-like cells (FIG. 1E). However, cells isolated from the other two subsets (i.e., K$^+$N$^+$A$^-$ and K$^+$N$^-$A$^-$) failed to exhibit high clonal proliferative potential. K$^+$N$^+$A$^+$ mesoderm-derived NRP-1$^+$CD31$^+$ cells produced robust in vivo human blood vessels filled with host murine red blood cells (FIG. 1F, top right panel; arrows point to blood vessels) similar to those produced by hiPSC-ECFC-like cells (FIG. 1F, top left panel). However, cells isolated from the other two subsets (i.e., K$^+$N$^+$A$^-$ and K$^+$N$^-$A$^-$) failed to produce robust in vivo human blood vessels filled with host murine red blood cells (FIG. 1F, bottom left and right panels, respectfully; arrows point to hCD31$^+$ functional blood vessels. Similarly, functional hCD31+ blood vessels were generated by K$^+$N$^+$A$^+$ mesoderm-derived NRP-1$^+$CD31$^+$ cells hiPSC-ECFC-like cells, but not by K$^+$N$^+$A$^-$ or K$^+$N$^-$A$^-$ mesoderm cells (FIG. 1G).

Figure 2A:
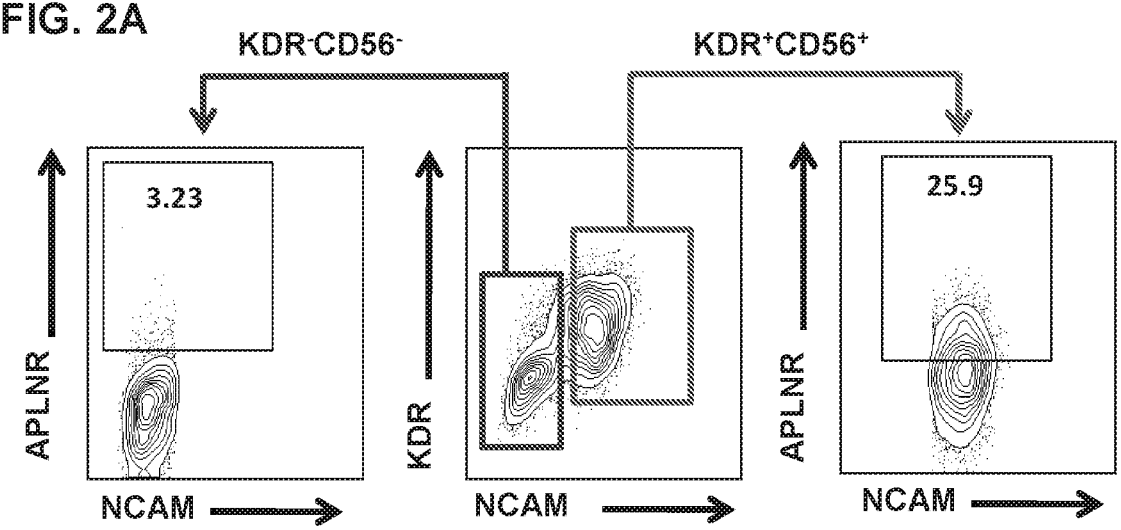
FIGS. 2A-2C illustrate that human iPS cells differentiated for 3-5 days using the protocol provided herein generate cells expressing mesoderm markers and lacking typical endothelial surface marker expression.
Figure 2B:
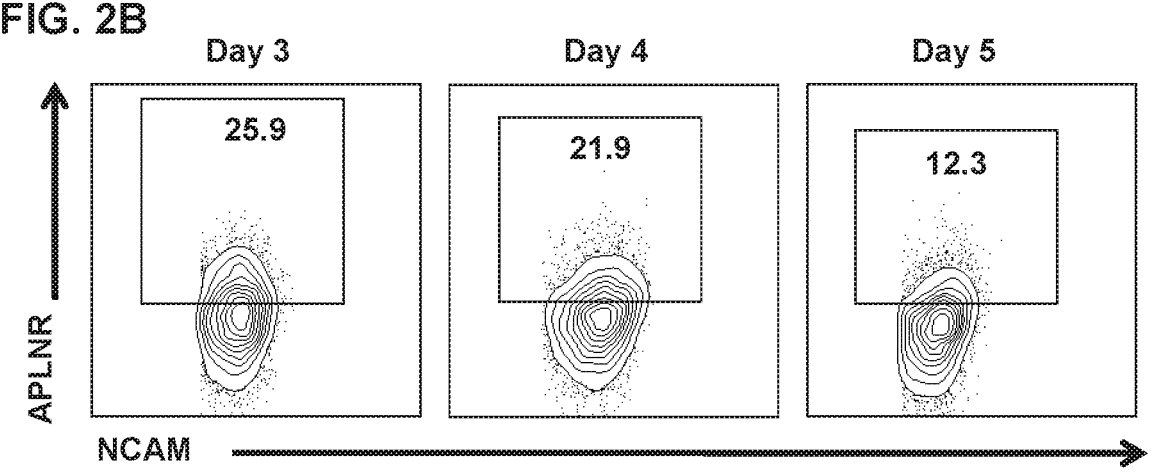
Figure 2C:
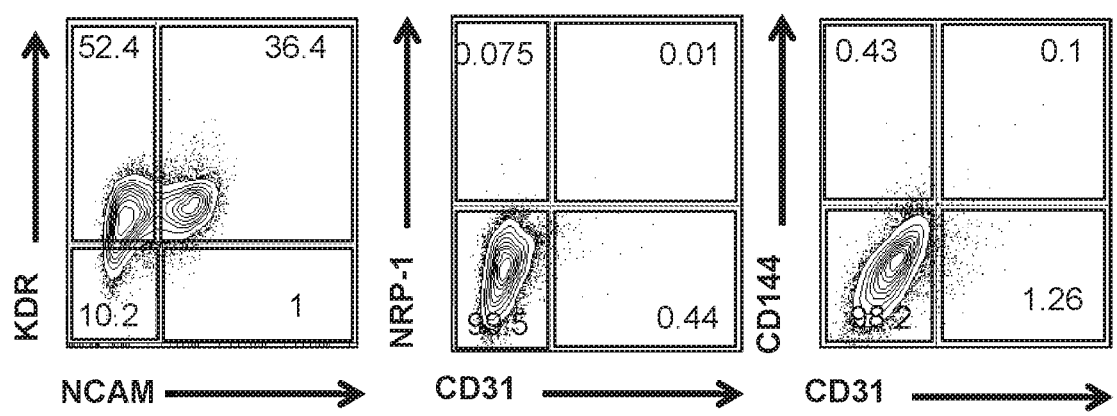

Referring now to FIGS. 2A-2C, human iPS cells after 3-5 days of differentiation using the above culture protocol generate cells expressing mesoderm markers and lacking typical endothelial surface expression. APLNR$^+$ cells were found only in the KDR$^+$NCAM$^+$ mesoderm sub-set and were absent in KDR$^-$NCAM$^-$ sub-set (FIG. 2A) and KDR$^+$ cells were found at highest levels at day 3 and 4 and decreased over time (FIG. 2B). Typical endothelial marker (CD31, NRP-1 and CD144) expression was not found in any day 4 differentiated cells (FIG. 2C).

Figure 3A:
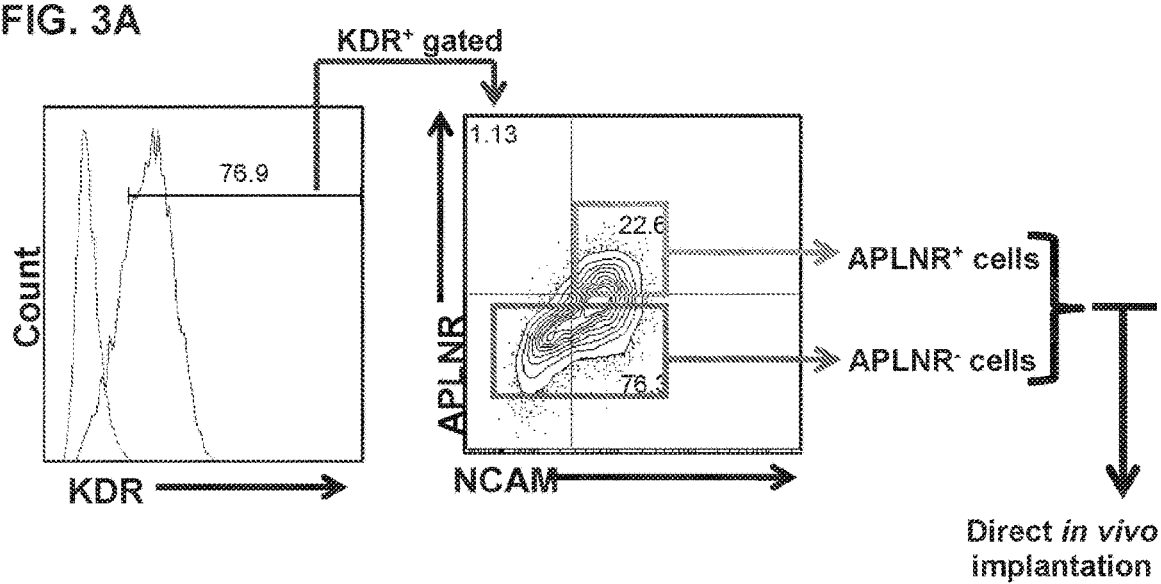
FIGS. 3A-3B illustrate that direct in vivo differentiation of D4 KNA+ mesoderm cells isolated without SSEA5 depletion formed robust human blood vessels and produced endoderm-derived cell-like derivatives.
Figure 3B:
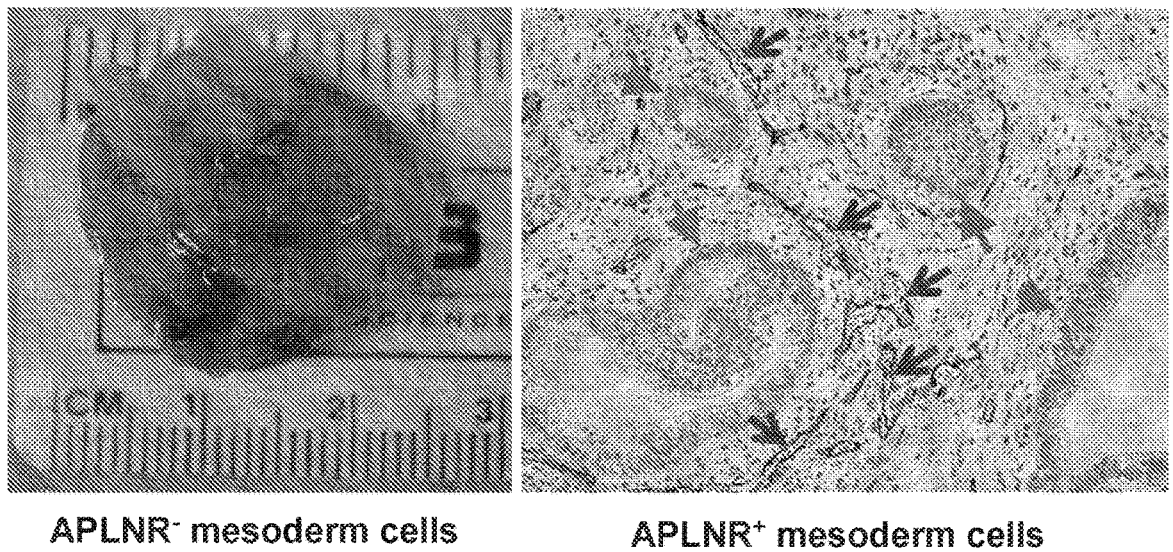

Referring now to FIGS. 3A-3B, direct in vivo differentiation of day 4 KNA$^+$ mesoderm cells that were isolated without selecting against SSEA5+ cells formed robust human blood vessels, but also produced endoderm-derived cell-like derivatives.

KDR$^+$ cells were gated for NCAM and APLNR expression. APLNR$^+$ and APLNR$^-$ mesoderm cells were sorted for further direct in vivo implantation and examination (FIG. 3A). Sorted APLNR$^-$ mesoderm cells produced teratomas after 2 months of in vivo implantation (FIG. 3B, left panel). The APLNR$^+$ mesoderm sub-set (FIG. 3B, right panel) formed robust in vivo human blood vessels filled with host murine red blood cells (blue open arrows) with accompanying endoderm-derived cell like derivatives (pink closed arrows).

Referring now to FIGS. 4A-4D, direct in vivo differentiation of D4 SSEA5 depleted KNA$^+$ mesoderm cells (i.e., SSEA5$^-$KDR$^+$NCAM$^+$APLNR$^+$, also referred to as SSEA5$^-$KNA$^+$) formed robust human blood vessels without giving rise to teratoma or endoderm-derived cell-like derivatives.

Figure 4A:
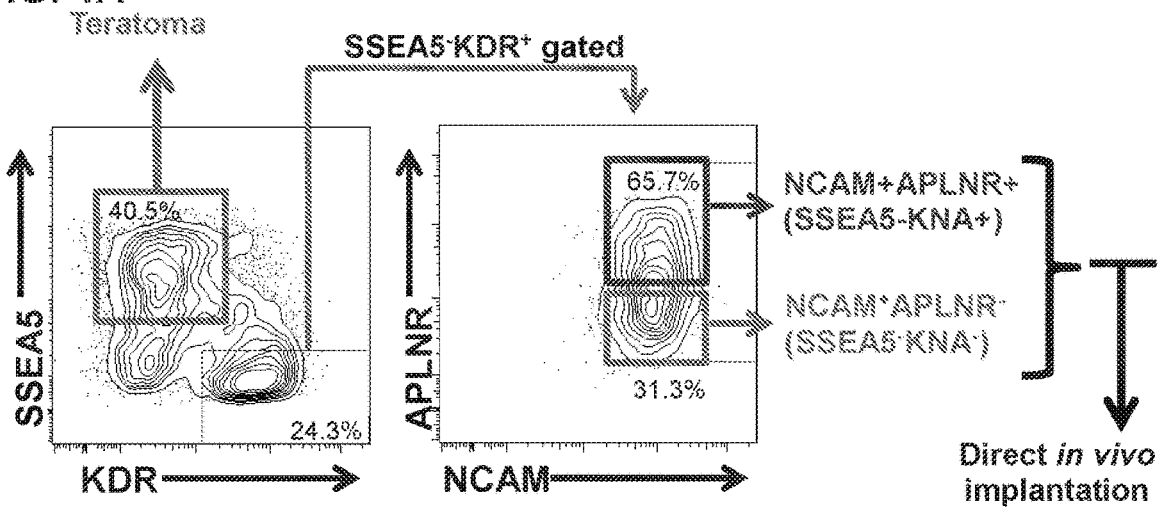
FIGS. 4A-4D illustrate direct in vivo differentiation of D4 SSEA5 depleted KNA+ mesoderm cells formed robust human blood vessels without giving rise to teratoma or endoderm-derived cell-like derivatives.
Figure 4B:
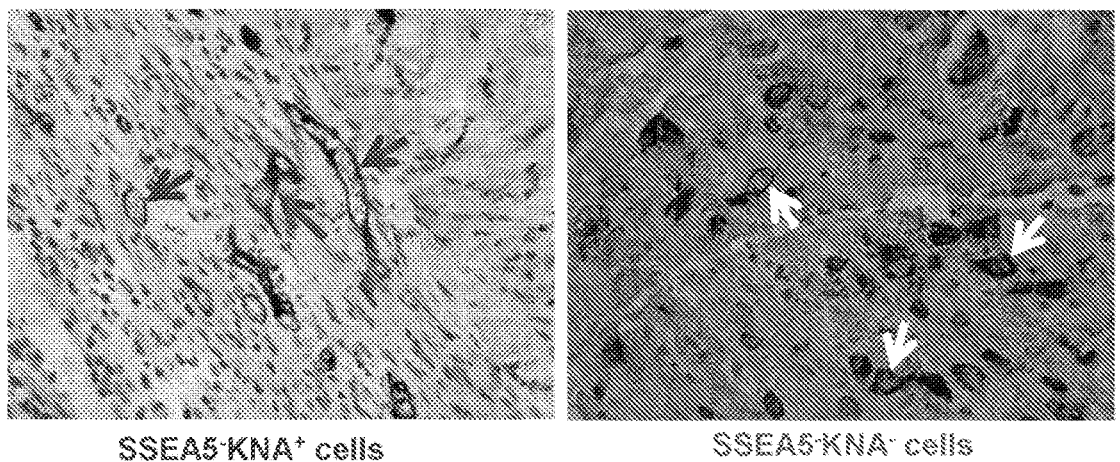
Figure 4C:
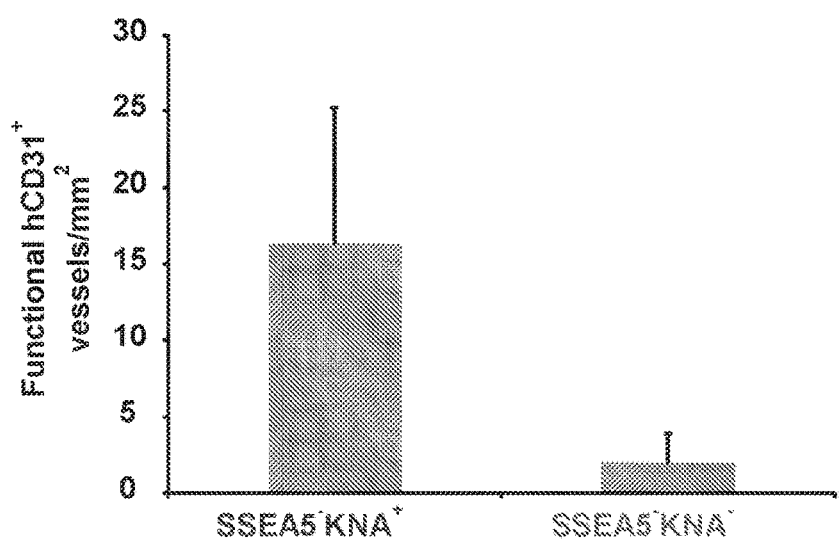
Figure 4D:
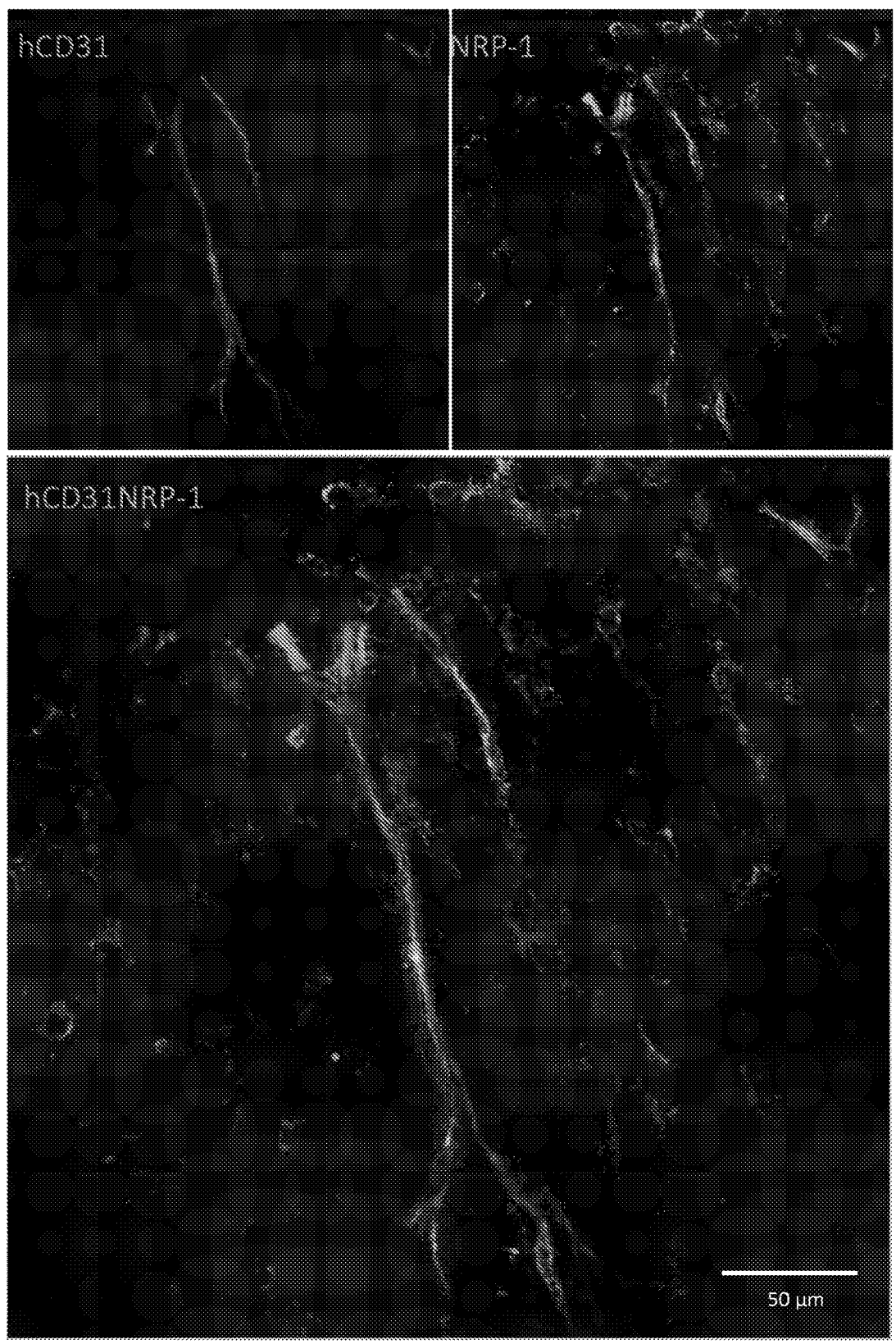

Day 4 differentiated hiPSCs were first gated for SSEA5 and KDR expression (FIG. 4A, left). The SSEA5$^-$KDR$^+$ cells were gated for NCAM and APLNR expression (FIG. 4A, right). SSEA5$^-$KDR$^+$NCAM$^+$APLNR$^+$ (SSEA5$^-$KNA$^+$) and SSEA5$^-$KDR$^+$NCAM$^+$APLNR$^-$ (SSEA5$^-$KNA$^-$) cells were sorted for further analysis. SSEA5$^-$KNA$^+$ cells formed robust functional in vivo vessels (FIG. 4B, blue arrows, left panel), SSEA5$^-$KNA$^-$ cells failed to form robust in vivo vessels (FIG. 4B, white arrows, right panel). Similarly, functional hCD31+ blood vessels were generated by SSEA5$^-$KNA$^+$ cells, but not by SSEA5$^-$KNA$^-$ cells (FIG. 4C). When implanted in vivo, SSEA5$^-$KNA$^+$ cells formed NRP-1$^+$CD31$^+$ ECFC vessels as early as 8 days after implantation (FIG. 4D).

Figure 5A:
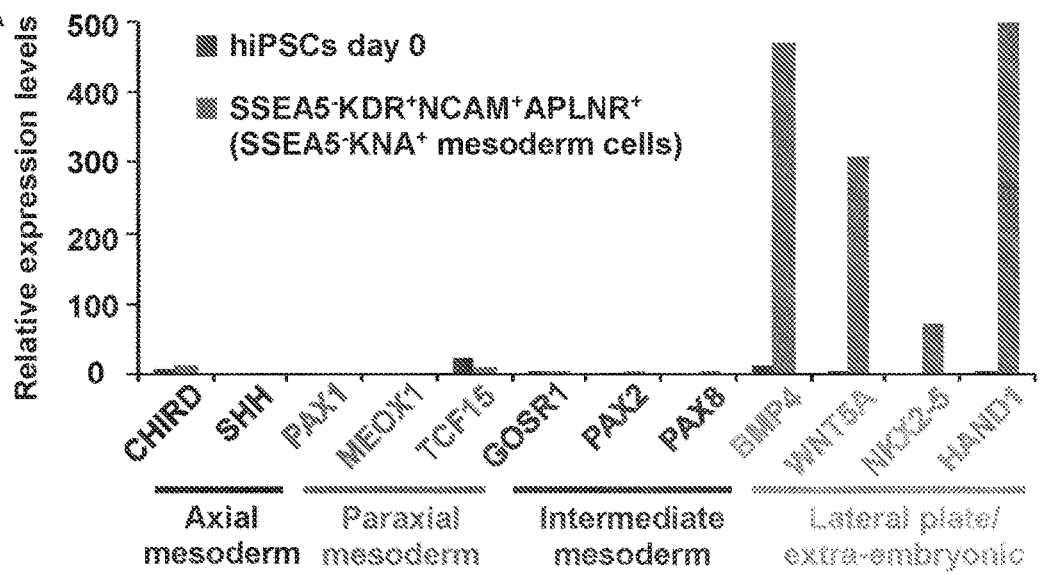
FIGS. 5A-5C illustrate that D4 SSEA5-depleted KNA+ mesoderm cells display transcripts typically enriched in lateral plate/extra-embryonic mesoderm cells, and exhibit enhanced formation of NRP-1+CD31+ cells with ECFC competence upon in vitro ECFC differentiation.
Figure 5B:
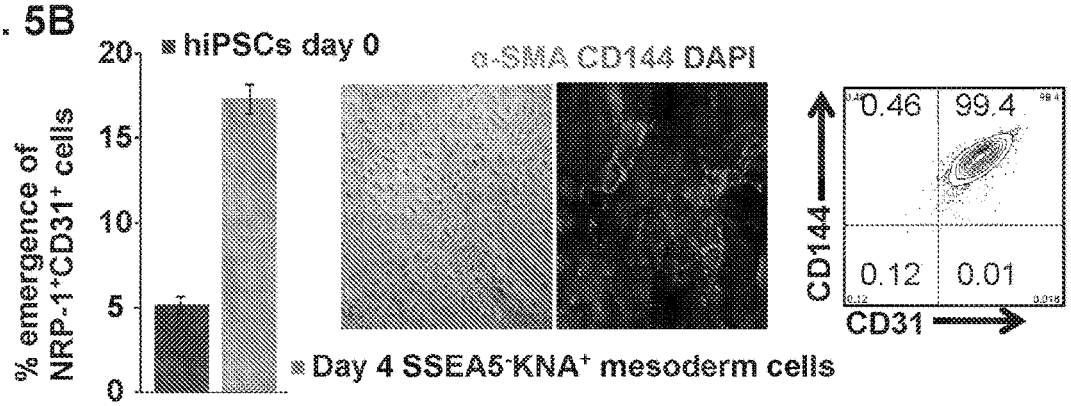
Figure 5C:
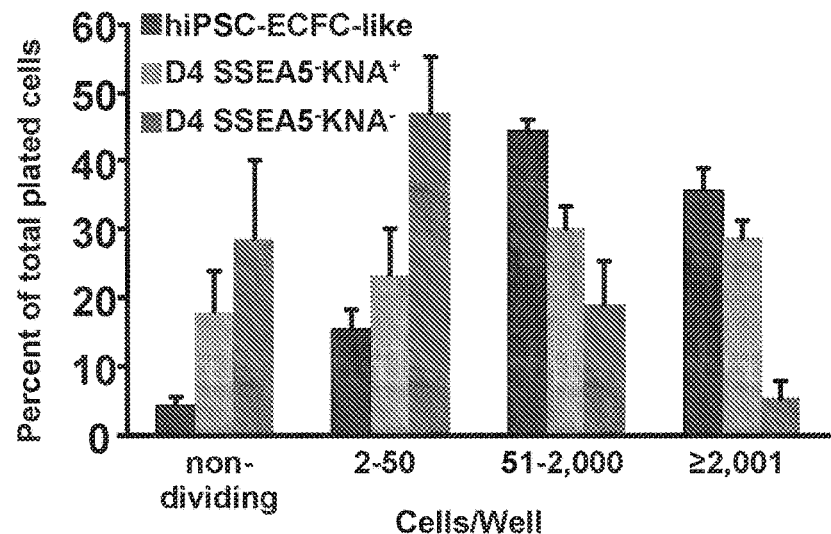

Referring now to FIGS. 5A-5C, day 4 SSEA5 depleted KNA$^+$ mesoderm cells displayed transcripts typically enriched in lateral plate/extra-embryonic mesoderm cells, and exhibited enhanced formation of NRP-1$^+$CD31$^+$ cells with ECFC competence upon in vitro ECFC differentiation.

Gene expression analysis revealed that SSEA5$^-$KNA$^+$ cells over-expressed lateral plate-extra-embryonic mesoderm markers, relative to hiPSCs, and lacked expression of axial, paraxial and intermediate mesoderm markers (FIG. 5A). Sorted SSEA5$^-$KNA$^+$ cells were further differentiated into the ECFC-like lineage for another 8 days (4 plus 8, total of 12 days). At day 12, SSEA5$^-$KNA$^+$ cells produced 3 fold more NRP-1$^+$CD31$^+$ cells compared to NRP-1$^+$CD31$^+$ cells produced from hiPSCs induced to differentiate into an ECFC-like lineage (i.e., 12 days differentiation without isolating a SSEA5$^-$KNA$^+$ mesoderm sub-set at day 4 of differentiation) (FIG. 5B; left panel, bar graph). NRP1$^+$CD31$^+$ cells derived from the SSEA5$^-$KNA$^+$ mesoderm cells formed a homogenous cobblestone endothelial monolayer (FIG. 5B, left middle panel), displayed uniform co-expression for CD31 and CD144 endothelial markers (FIG. 5B, right panel) and completely lacked α-SMA expression (FIG. 5B, right middle panel), suggesting that the SSEA5⁻KNA⁺ mesoderm cells were able to differentiate into a stable ECFC-like phenotype. SSEA5⁻KNA⁺ mesoderm-derived NRP-1⁺CD31⁺ cells exhibited high clonal proliferative potential with a hierarchy of colonies ranging from clusters of 2-50 cells up to colonies of >2001 similar to that of hiPSC-ECFCs (FIG. 5C). However, cells isolated from SSEA5⁻KNA⁻ mesoderm sub-set failed to exhibit high clonal proliferative potential (FIG. 5C).

Referring now to FIGS. 6A-6G, the inventors found that Fc-NRP-1 mediates VEGF-KDR signaling through $p130^{cas}$/Pyk2 activation and enhances formation of SSEA5⁻KNA⁺ mesoderm cells from hiPSCs.

Figure 6A:
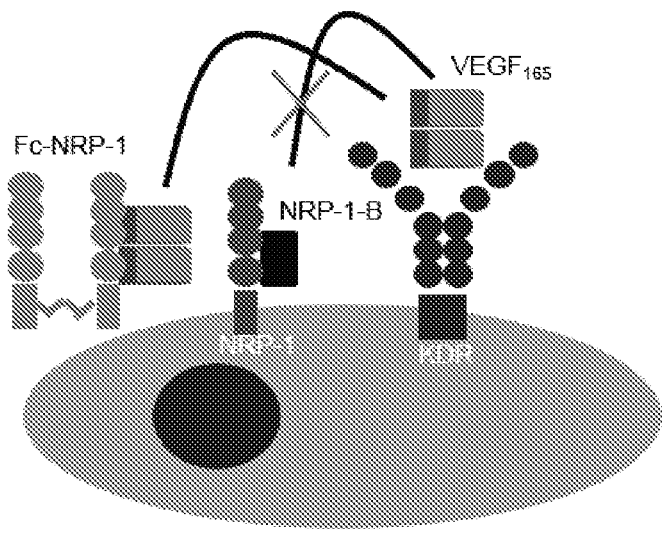
FIGS. 6A-6G illustrate that Fc-NRP-1 mediates VEGF-KDR signaling through p130$^{cas}$/Pyk2 activation and enhances formation of SSEA5−KNA+ mesoderm cells from hiPSCs.

NRP-1, KDR, Fc-NRP-1, NRP-1-B and $VEGF_{165}$ functions in endothelial cells are shown in FIG. 6A. Briefly, NRP-1 functions as a $VEGF_{165}$ co-receptor and brings $VEGF_{165}$ to its receptor (KDR). Fc-NRP-1 acts as surrogate for membrane NRP-1 and binds and brings $VEGF_{165}$ to KDR. In contrast, NRP-1-B blocking antibody selectively binds to the $VEGF_{165}$ binding site of NRP-1, thereby specifically blocking binding of $VEGF_{165}$ to NRP-1.

Figure 6B:
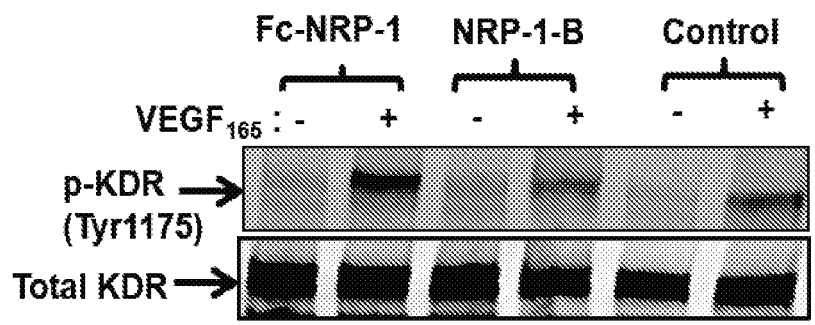
Figure 6C:
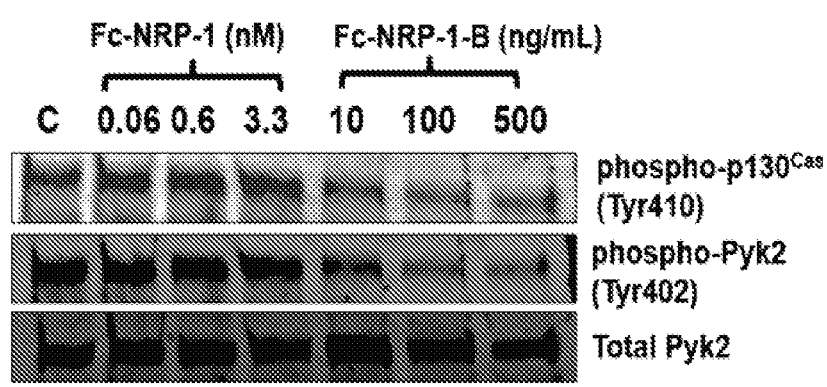

Examination of KDR and $p130^{cas}$/Pyk2 phosphorylation was carried out by Western blotting (FIGS. 6B and 6C). KDR phosphorylation was observed in VEGF stimulated groups and Fc-NRP-1 dimer treatment increased phosphorylation of KDR compared to control treated cells. However, decreased phosphorylation was observed in NRP-1-B treated cells. Similarly, increased $p130^{cas}$/Pyk2 phosphorylation was observed in Fc-NRP-1 dimer treated cells compared to NRP-1-B treated cells.

Figure 6D:
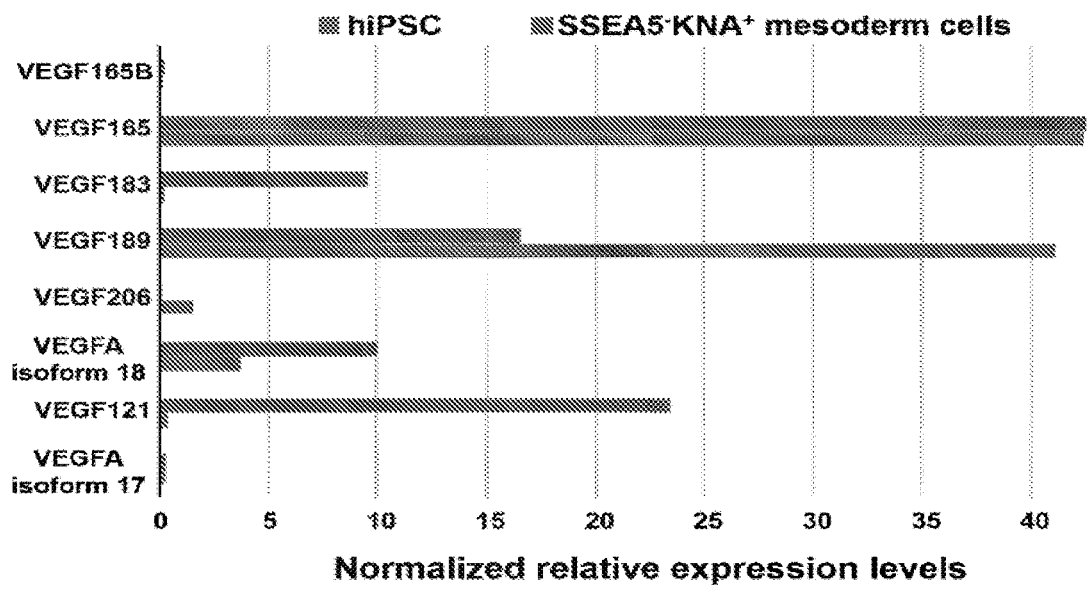
Figure 6E:
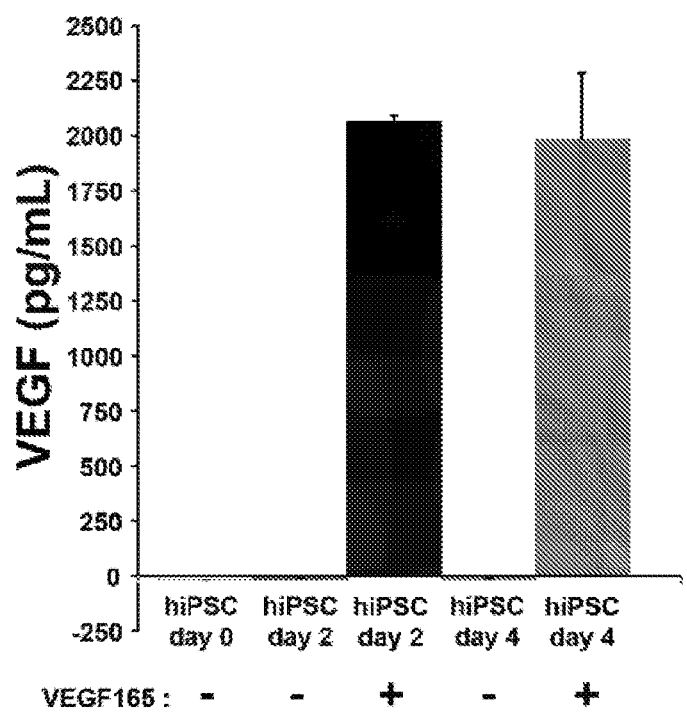

Gene expression of VEGF-A isoforms in hiPSCs and SSEA5⁻KNA⁺ mesoderm cells was investigated. VEGF-A isoforms were not up-regulated in SSEA5⁻KNA⁺ mesoderm cells compared to hiPSCs (FIGS. 6D and 6E).

Figure 6F:
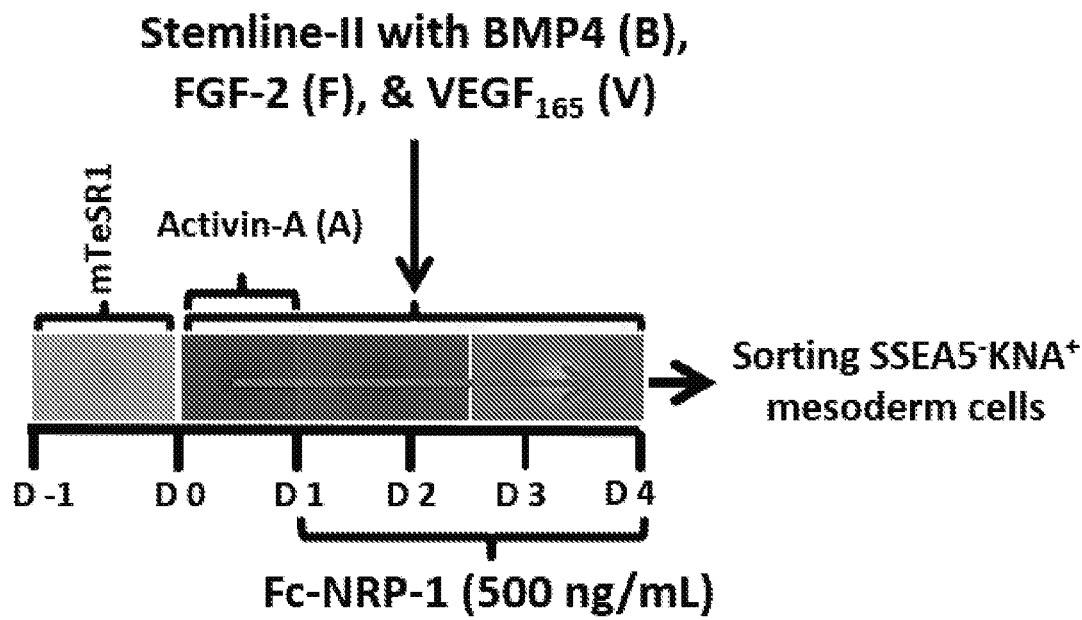
Figure 6G:
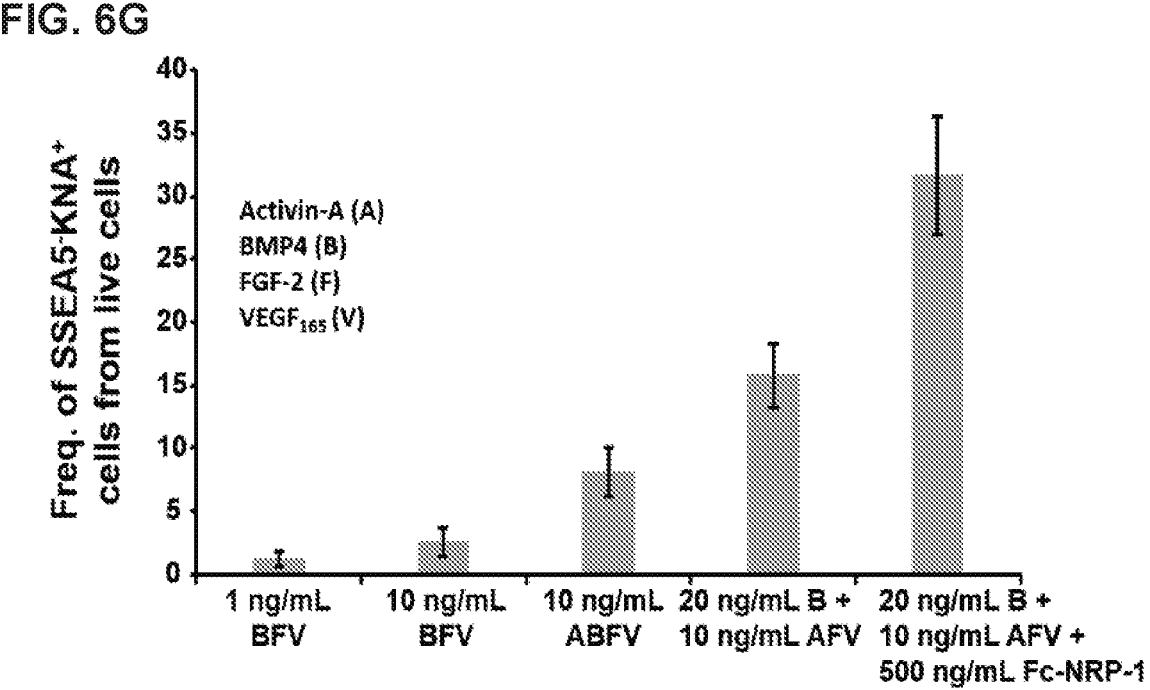

A mesoderm lineage differentiation protocol that involves culturing the cells undergoing mesoderm induction in the presence of Fc-NRP-1 dimer and growth factors is shown in FIG. 6F. Dimeric Fc-NRP-1 treatment to differentiating hiPSCs caused more than a 2-fold increase in the production of SSEA5⁻KNA⁺ mesoderm cells compared to Fc-NRP-1-untreated cells (FIG. 6G).

Referring now to FIGS. 7A-7E, specific miRNA mimics miRNA inhibitors and combinations thereof enhance SSEA5⁻KNA⁺ mesoderm formation from hiPSCs.

Figure 7A:
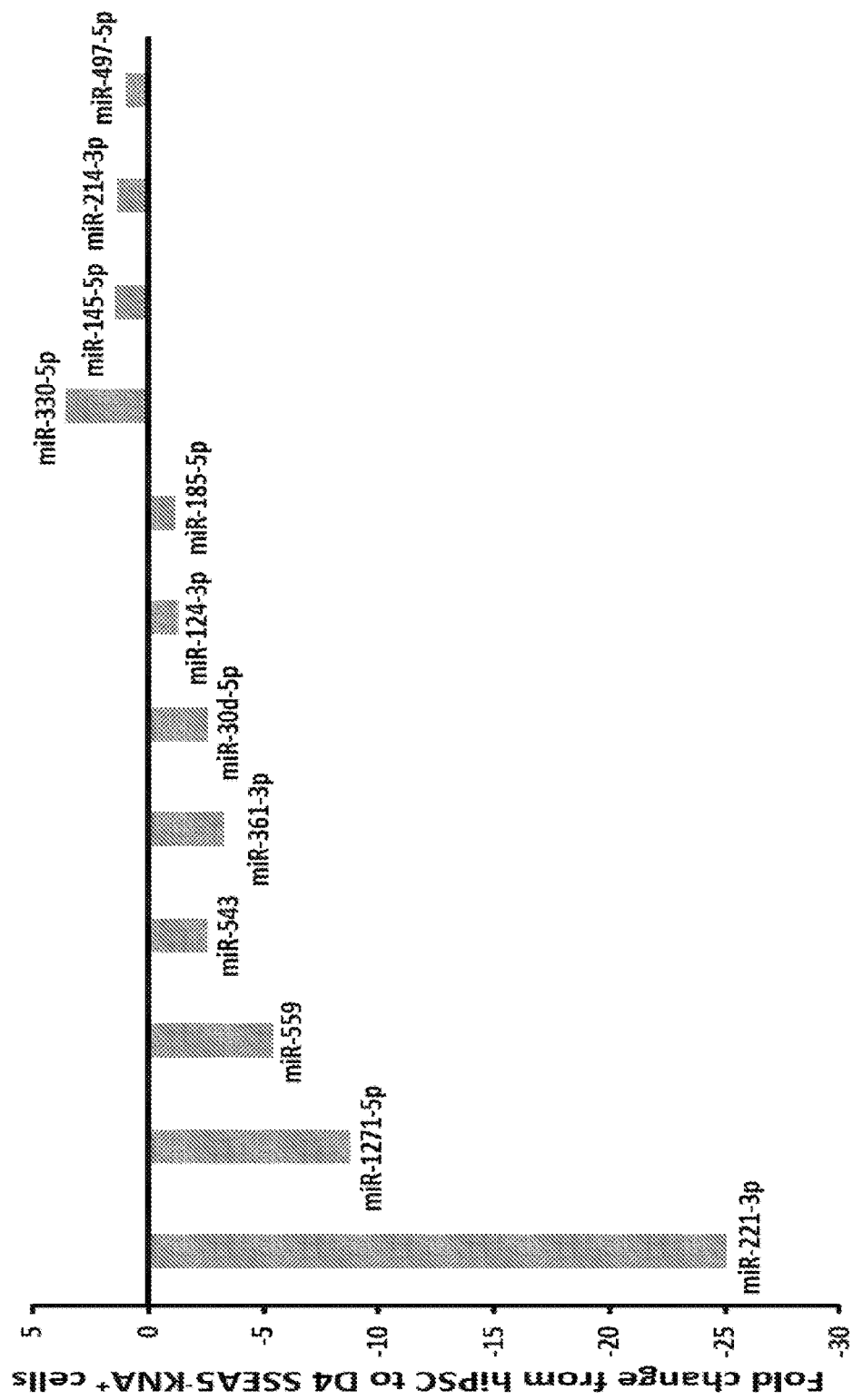
FIGS. 7A-7E illustrate that specific miRNA mimics and inhibitors enhance SSEA5−KNA+ mesoderm generation from hiPSCs.

In order to identify miRNAs and their putative transcription factor targets relevant to SSEA5⁻KNA⁺ mesoderm formation, we performed miRNA micro-array and RNA-seq analysis of Day 0 undifferentiated hiPSCs and Day 4 SSEA5⁻KNA⁺ mesoderm cells (FIG. 7A). Our analysis of expression of miRNA and mRNA transcripts revealed 12 miRs (miR-221-3p, miR-1271-5p, miR-559, miR-543, miR-361-3p, miR-30d-5p, miR-124-3p, miR-185-5p, miR-330-5p, miR-145-5p, miR-214-3p and miR-497-5p) with published and validated targets that potentially regulate transcription factors relevant to SSEA5⁻KNA⁺ mesoderm formation from hiPSCs. Among these 12 candidate miRNAs, we found 8 miRNAs (miR-221-3p, miR-1271-5p, miR-559, miR-543, miR-361-3p, miR-30d-5p, miR-124-3p and miR-185-5p) were expressed at lower levels in Day 4 SSEA5⁻KNA⁺ mesoderm cells compared to Day 0 undifferentiated hiPSCs, and four miRNAs (miR-330-5p, miR-145-5p, miR-214-3p and miR-497-5p) were expressed at higher levels in Day 4 SSEA5⁻KNA⁺ mesoderm cells compared to Day 0 undifferentiated hiPSCs.

Figure 7B:
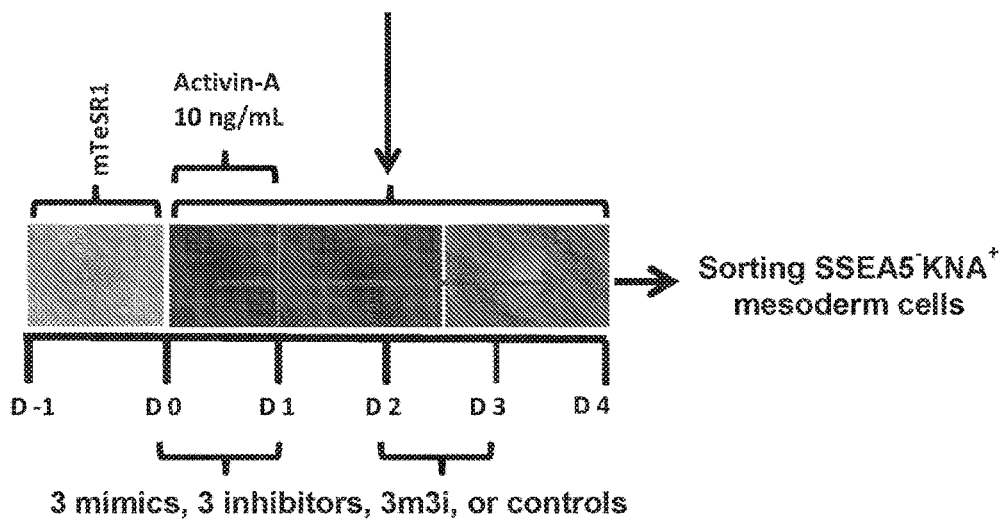
Figure 7C:
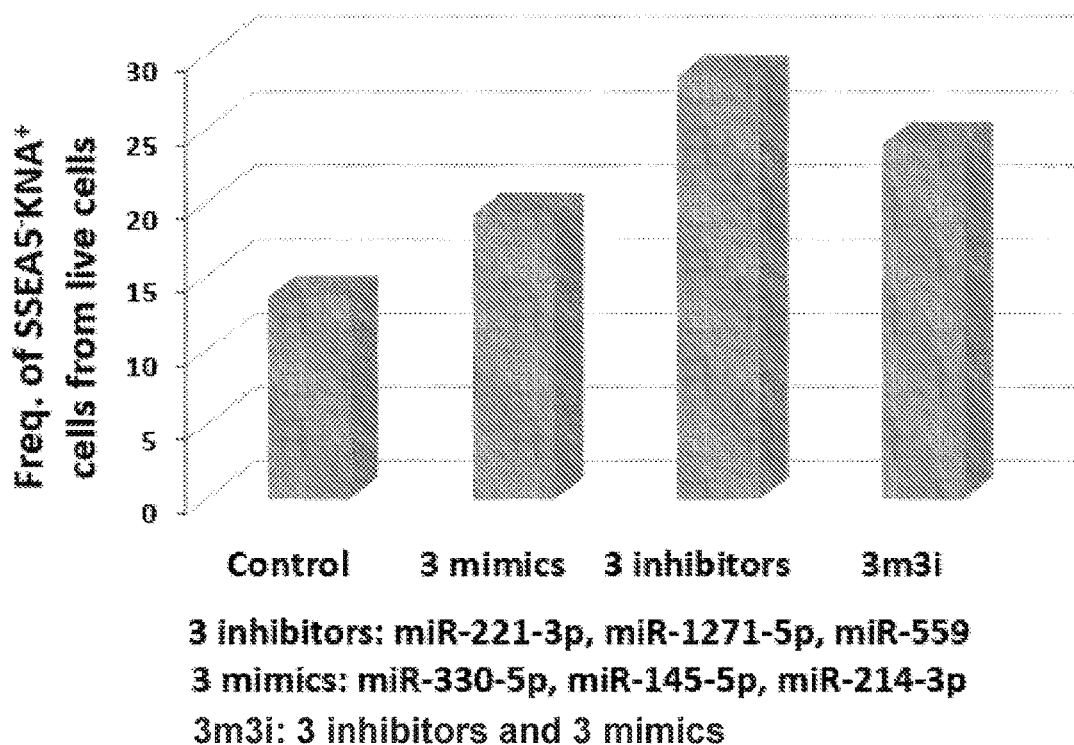
Figure 7D:
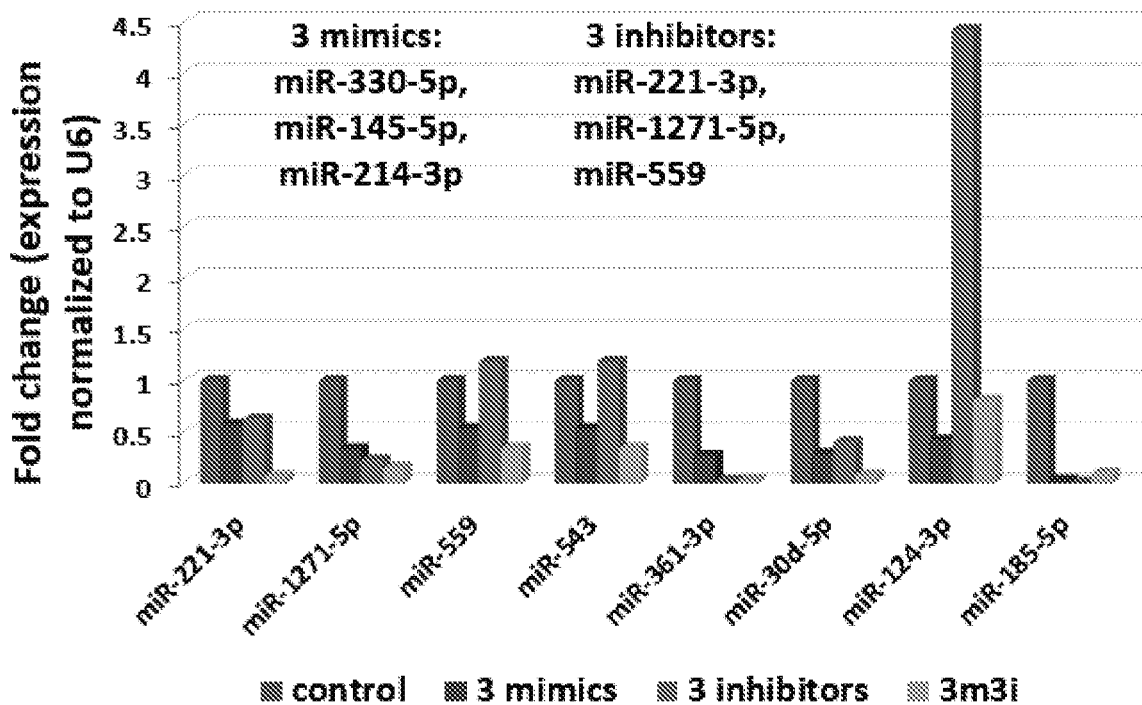
Figure 7E:
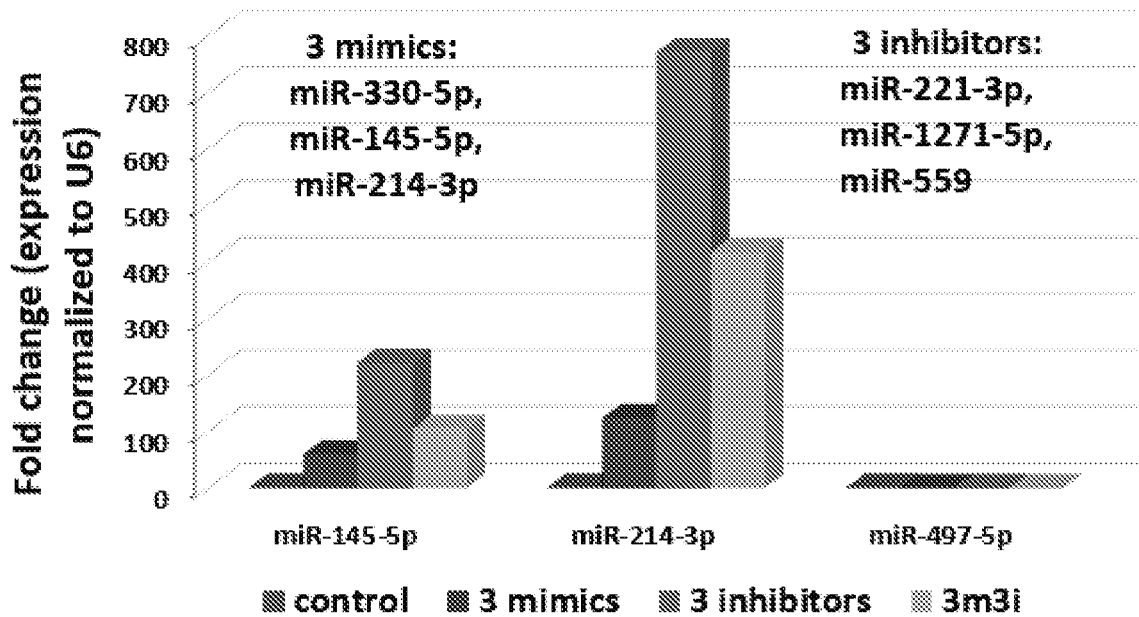

To determine the effect of mimicking and/or inhibiting the identified miRNAs on mesoderm lineage differentiation, we developed a protocol for inducing mesoderm generation from hiPSCs in the presence of specific miRNA mimics, miRNA inhibitors, both mimics and inhibitors (3m3i), or mimic/inhibitor controls (FIG. 7B). Addition of specific mimics for 3 miRNAs (miR-330-5p, miR-145-5p and miR-214-3p), specific inhibitors for 3 miRNAs (miR-221-3p, miR-1271-5p, miR-559) or 3 mimics and 3 inhibitors combined increased the frequency of SSEA5⁻KNA⁺ mesoderm cells compared to the control (FIG. 7C). Addition of these specific mimics, inhibitors, or 3m3i decreased the expression of most of the miRNAs that were identified (in our miRNA array analysis) to be expressed at lower levels in Day 4 SSEA5⁻KNA⁺ mesoderm cells (FIG. 7D). Addition of these specific mimics, inhibitors or 3m3i increased the expression of some of the miRNAs that were identified (in our miRNA array analysis) to be expressed at higher levels in Day 4 SSEA5⁻KNA⁺ mesoderm cells (FIG. 7E).

Referring now to FIGS. 8A-8D, miR-214-3p targets CLDN6 in differentiating hiPSC and enhances formation of SSEA5⁻KNA⁺ mesoderm cells.

Figure 8A:
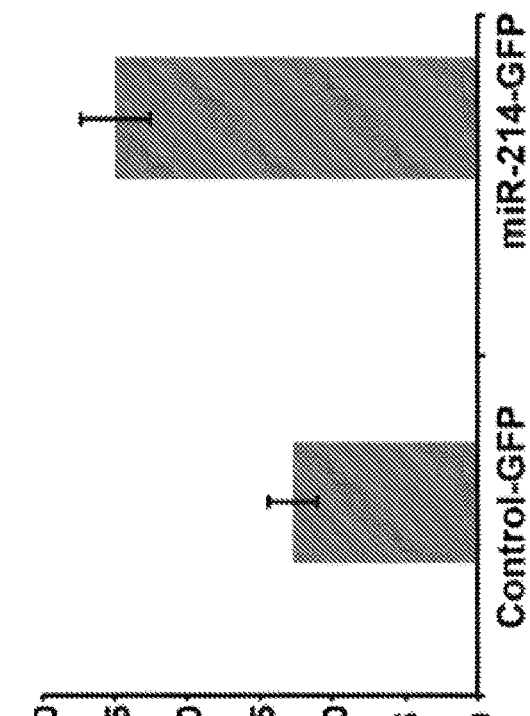
FIGS. 8A-8D illustrate that miR-214-3p targets CLDN6 in differentiating hiPSC and enhances formation of SSEA5−KNA+ mesoderm cells.
Figure 8B:
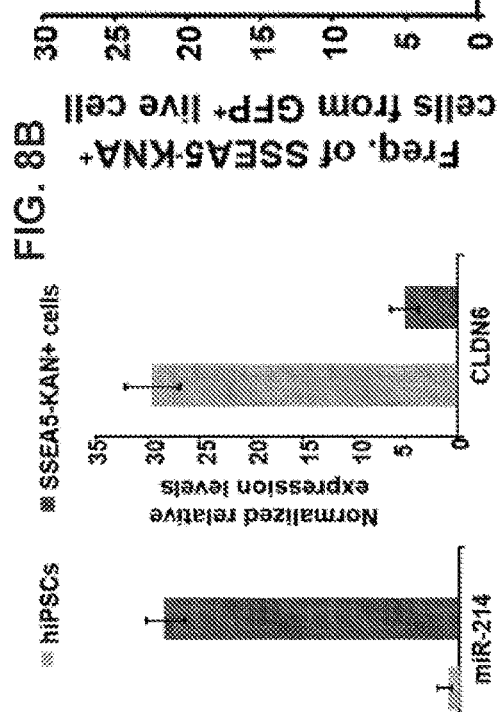
Figure 8C:
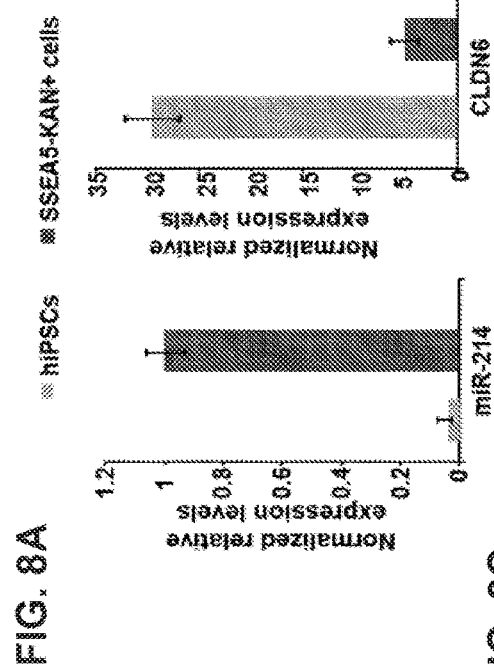
Figure 8D:
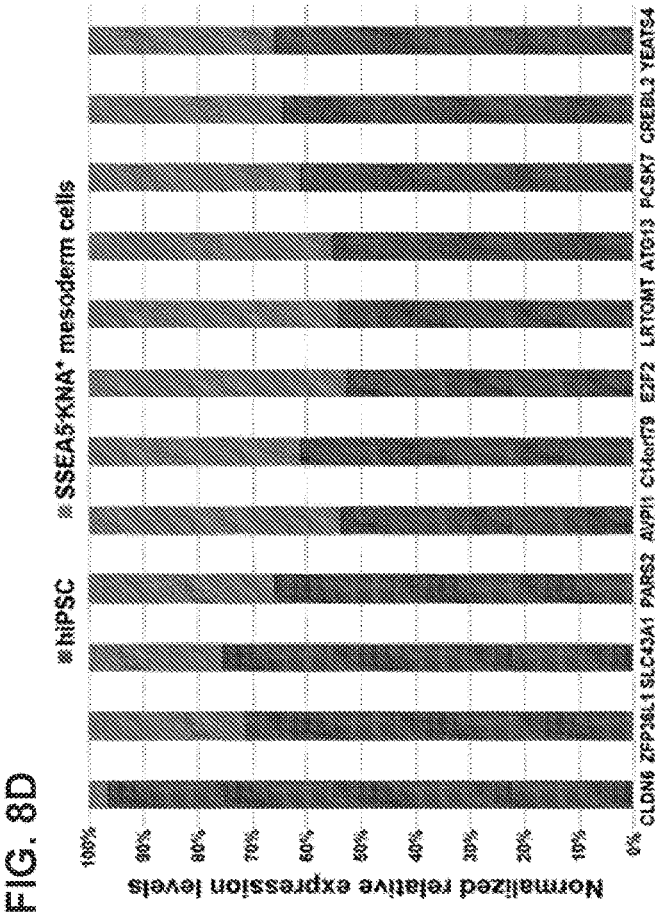
Figure 8D:
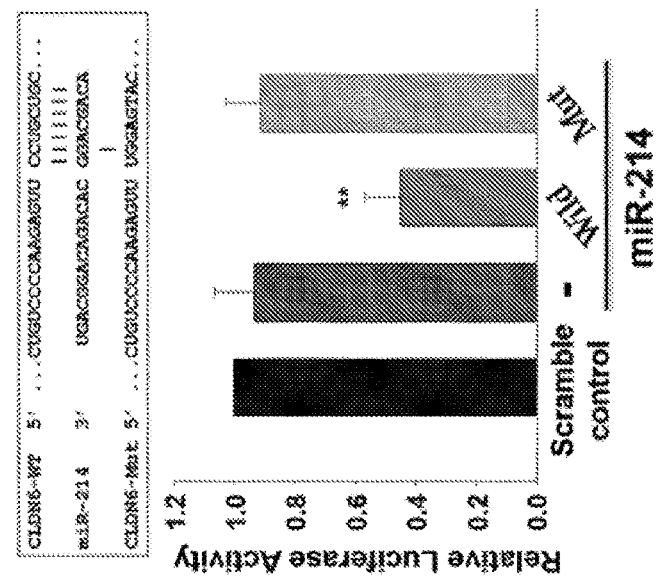

Expression of miR-214 and its putative target CLDN6 was analyzed in hiPSCs and SSEA5⁻KNA⁺ mesoderm cells. We found that miR-214 and CLDN6 exhibit an inverse expression correlation in hiPSCs and SSEA5⁻KNA⁺ mesoderm cells, respectively (FIG. 8A). miR-214 is highly expressed in SSEA5⁻KNA⁺ cells compared to hiPSCs (FIG. 8A, left bar) and CLDN6 is expressed at lower levels in SSEA5⁻KNA⁺ cells compared to hiPSCs (FIG. 8A, right bar). Over-expression of miR-214 in differentiating hiPSCs caused more than a 2-fold increase in the production of SSEA5⁻KNA⁺ mesoderm cells compared to a GFP reporter control vector (FIG. 8B). A luciferase reporter assay confirmed that miR-214 directly regulates expression of wild type (WT) CLND6 (FIG. 8C). Differential gene expression analysis between hiPSC and SSEA5⁻KNA⁺ mesoderm cells revealed that CLND6 is one of the most down-regulated genes among the 12 validated miR-214 targets that decreased in the SSEA5⁻KNA⁺ mesoderm (FIG. 8D). For example, CLDN6 is only expressed at only 4% in the SSEA5⁻KNA⁺ mesoderm cells compared to the level measured in the hiPSCs.

Although the disclosure has been described with reference to certain specific embodiments, various modifications thereof will be apparent to those skilled in the art without departing from the purpose and scope of the disclosure as outlined in the claims appended hereto. Any examples provided herein are included solely for the purpose of illustrating the disclosure and are not intended to limit the disclosure in any way. Any drawings provided herein are solely for the purpose of illustrating various aspects of the disclosure and are not intended to be drawn to scale or to limit the disclosure in any way. The disclosures of all prior art recited herein are incorporated herein by reference in their entirety.

We claim:

1. A method for generating an isolated population of human KDR⁺NCAM⁺APLNR⁺ mesoderm cells from human pluripotent stem cells, the method comprising:
   (a) providing pluripotent stem cells (PSCs);
   (b) inducing the pluripotent stem cells to undergo mesodermal differentiation, wherein the mesodermal induction is carried out in the absence of co-culture cells and further comprises:
      i) culturing the pluripotent stem cells for about 24 hours in a mesoderm differentiation medium comprising Activin A, bone morphogenetic protein-4 (BMP-4), vascular endothelial growth factor (VEGF) and fibroblast growth factor (FGF-2); and ii) replacing the medium of step i) with a mesoderm differentiation medium comprising BMP-4, VEGF and FGF-2 about every 24-48 hours thereafter for about 72 hours; and (c) isolating from the cells induced to undergo differentiation the mesoderm cells, wherein the isolation of mesoderm cells comprises:

iii) sorting the mesoderm cells to select for KDR$^+$ NCAM$^-$APLNR$^+$ cells, wherein step i) and/or step ii) of step (b) comprises contacting the cells with one or more of a miRNA inhibitor selected from the group consisting of miR-211-3p, miR-1271-5p, miR-559, miR-543, miR-361-3p, miR-30d-5p, miR-124-3p and miR-185-5p and/or one or more of a miRNA mimic selected from the group consisting of miR-330-5p, miR-145-5p, and miR-497-5p.

2. The method of claim 1, wherein the sorting further comprises selection of SSEA5$^-$ KDR$^+$NCAM$^+$APLNR$^+$ cells.

3. The method of claim 1, wherein the mesodermal induction of step (b) further comprises contacting the cells undergoing mesodermal induction with Fc Neuropilin-1 (Fc-NRP-1).

4. The method of claim 3, wherein the Fc-NRP-1 is added to the mesoderm differentiation medium of step (b) ii).

5. The method of claim 1, wherein the miRNA inhibitor inhibits an miRNA selected from the group consisting of: miR-221-3p, miR-1271-5p, and miR-559.

6. The method of claim 1, wherein the cells undergoing mesodermal induction are contacted with miR-221-3p.

7. The method of claim 1, wherein the miRNA mimic mimics miR-330-5p.

8. The method of claim 6, wherein the cells undergoing mesodermal induction are cultured with one or more of an miRNA mimic of miR-330-5p or miR-145-5p.

9. The method of claim 1, further comprising: inducing the isolated mesoderm cells to undergo endothelial differentiation, wherein the endothelial induction comprises:
culturing the isolated mesoderm cells in an endothelial differentiation medium comprising BMP-4, VEGF and FGF-2 for about 6-8 days; and
isolating from the cells induced to undergo endothelial differentiation endothelial colony forming-like (ECFC-like) cells, wherein the ECFC-like cells are CD31+ NRP-1+ and exhibit a cobblestone morphology.

10. The method of claim 9, wherein the isolated ECFC-like cells are further characterized by one or more of CD144+, KDR+ and alpha-SMA-expression.

* * * * *